US006284698B1

(12) United States Patent
Chen et al.

(10) Patent No.: US 6,284,698 B1
(45) Date of Patent: Sep. 4, 2001

(54) HIGHLY ACTIVATED BIMETALLIC COMPLEXES AND POLYMERIZATION PROCESS

(75) Inventors: Eugene Y. Chen; Shaoguang S. Feng; David D. Graf; Jasson T. Patton, all of Midland, MI (US); David R. Wilson, Leipzig (DE)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/528,787

(22) Filed: Mar. 17, 2000

Related U.S. Application Data

(63) Continuation-in-part of application No. 09/234,192, filed on Jan. 20, 1999, which is a continuation-in-part of application No. 09/141,659, filed on Aug. 28, 1998, now Pat. No. 6,153,776.

(60) Provisional application No. 60/092,294, filed on Jul. 10, 1998, and provisional application No. 60/060,712, filed on Sep. 15, 1997.

(51) Int. Cl.[7] .............................. B01J 31/00; B01J 37/00; C08F 4/02; C08F 4/60

(52) U.S. Cl. ........................ 502/102; 502/103; 502/113; 502/117; 502/152; 502/155

(58) Field of Search .................................. 502/103, 112, 502/152, 155, 113

(56) References Cited

U.S. PATENT DOCUMENTS

| | | |
|---|---|---|
| 3,242,099 | 3/1966 | Manyik et al. . |
| 5,055,438 | 10/1991 | Canich . |
| 5,057,475 | 10/1991 | Canich et al. . |
| 5,064,802 | 11/1991 | Stevens et al. . |
| 5,096,867 | 3/1992 | Canich . |
| 5,198,401 | 3/1993 | Turner et al. . |
| 5,372,980 * | 12/1994 | Davis .................... 502/117 |
| 5,374,696 | 12/1994 | Rosen et al. . |
| 5,470,993 | 11/1995 | Devore et al. . |
| 5,585,508 * | 12/1996 | Kuber et al. .......... 502/152 |
| 5,627,117 * | 5/1997 | Mukaiyama et al. ............. 502/113 |
| 5,770,666 * | 6/1998 | Hamura et al. .............. 502/117 |
| 5,854,165 * | 12/1998 | Yabunouchi et al. .......... 502/117 |
| 5,892,078 * | 4/1999 | Gores et al. ............ 502/117 |
| 5,892,079 * | 4/1999 | Wilson, Jr. ............. 502/117 |
| 5,962,359 * | 10/1999 | Aulbach et al. ............. 502/117 |
| 6,010,974 * | 1/2000 | Kim et al. ............... 502/152 |
| 6,096,677 * | 8/2000 | Wilson, Jr. ............. 502/117 |
| 6,143,682 * | 11/2000 | Fisher .................. 502/117 |
| 6,153,776 * | 11/2000 | Patton et al. ............ 502/117 |
| 6,171,994 * | 1/2001 | Yabunouchi et al. .......... 502/155 |
| 6,184,402 * | 2/2001 | Yamazaki et al. ............ 502/103 |
| 6,191,284 * | 2/2001 | Knochel et al. ........... 502/155 |

FOREIGN PATENT DOCUMENTS

| | | |
|---|---|---|
| 416815 | 7/1990 | (EP) . |
| 739 897 | 10/1996 | (EP) . |
| 779 295 | 6/1997 | (EP) . |

OTHER PUBLICATIONS

Chemical Abstract, vol. 120, No. 3, Jan. 17, 1994, Abstract No. 30861v, Elschenbroich, et al.

Organomet. Chem., vol. 460, pp. 191–195 (1993), S. Jungling et al. no month.

* cited by examiner

*Primary Examiner*—Elizabeth D. Wood
*Assistant Examiner*—J. Pasterczyk

(57) ABSTRACT

Catalyst compositions comprising 1) one or more bimetallic Group 3–6 or Lanthanide metal complexes corresponding to the formula:

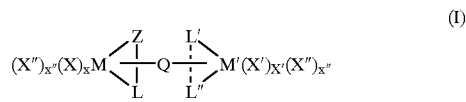

(I)

wherein:

M and M' are independently Group 3, 4, 5, 6, or Lanthanide metals;

L is a divalent group (or trivalent group if bound to Q) having up to 50 nonhydrogen atoms and containing an aromatic π-system through which the group is bound to M, said L also being bound to Z;

L' is a monovalent group or a divalent group (if bound to L" or Q), or a trivalent group (if bound to both L" and Q) having up to 50 nonhydrogen atoms and containing an aromatic π-system through which the group is bound to M';

L" is a monovalent group or a divalent group (if bound to L' or Q), or a trivalent group (if bound to both L' and Q) having up to 50 nonhydrogen atoms and containing an aromatic π-system through which the group is bound to M', or L" is a moiety comprising boron or a member of Group 14 of the Periodic Table of the Elements, and optionally also comprising nitrogen, phosphorus, sulfur or oxygen, said L" having up to 20 non-hydrogen atoms;

Z is a moiety comprising boron or a member of Group 14 of the Periodic Table of the Elements, and also comprising nitrogen, phosphorus, sulfur or oxygen, said Z having up to 20 non-hydrogen atoms;

X, X' and X" are as defined in the specification;

Q is a divalent anionic ligand group bound at one terminus to either Z or L and bound at the remaining terminus to either L' or L", said Q having up to 20 nonhydrogen atoms; and x, x', and x" are independently integers from 0 to 3; and 2) one or more activating cocatalysts;

wherein activating cocatalyst component 2) causes both metal centers, M and M', of the one or more bimetallic metal complexes 1) to be catalytically active for the polymerization of addition polymerizable monomers.

11 Claims, No Drawings

HIGHLY ACTIVATED BIMETALLIC COMPLEXES AND POLYMERIZATION PROCESS

CROSS-REFERENCE TO RELATED APPLICATION

This application is a continuation-in-part of U.S. Ser. No. 09/234,192, filed Jan. 20, 1999, allowed, which is a continuation-in-part of U.S. Ser. No. 09/141,659, filed Aug. 28, 1998, now U.S. Pat. No. 6,153,776 which in turn claims benefit of priority from Provisional application 60/060,712, filed Sep. 15, 1997 and from Provisional application 60/092,294, filed Jul. 10, 1998.

BACKGROUND OF THE INVENTION

This invention relates to certain Group 3, 4 or Lanthanide metal complexes possessing two metal centers in which both metal centers are activated so as to possess at least partial ligand separation or ion formation. The invention further relates to polymerization catalysts comprising the foregoing metal complexes possessing two metal centers, use thereof in addition polymerizations to prepare olefin polymers, and the resulting olefin polymers, particularly polymers having improved physical properties.

Biscyclopentadienyl Group 4 transition metal complexes in which the metal is in the +4, +3 or +2 formal oxidation state, and olefin polymerization catalysts formed from such by combination with an activating agent, for example, alumoxane or ammonium borate, are well known in the art. Thus, U.S. Pat. No. 3,242,099 describes the formation of olefin polymerization catalysts by the combination of bis-cyclopentadienyl metal dihalides with alumoxane. U.S. Pat. No. 5,198,401 discloses tetravalent biscyclopentadienyl Group 4 transition metal complexes and olefin polymerization catalysts obtained by converting such complexes into cationic forms in combination with a non-coordinating anion. Particularly preferred catalysts are obtained by the combination of ammonium borate salts with the biscyclopentadienyl titanium, zirconium or hafnium complexes. Among the many suitable complexes disclosed are bis(cyclopentadienyl)zirconium complexes containing a diene ligand attached to the transition metal through σ-bonds where the transition metal is in its highest formal oxidation state. R. Mülhaupt, et al., *J. Organomet. Chem.*, 460, 191 (1993), reported on the use of certain binuclear zirconocene derivatives of dicyclopentadienyl-1,4-benzene as catalysts for propylene polymerization.

Constrained geometry metal complexes, including titanium complexes, and methods for their preparation are disclosed in U.S. application Ser. No. 545,403, filed Jul. 3, 1990 (EP-A-416,815); U.S. Pat. No. 5,064,802, U.S. Pat. No. 5,374,696, U.S. Pat. No. 5,055,438, U.S. Pat. No. 5,057,475, U.S. Pat. No. 5,096,867, and U.S. Pat. No. 5,470,993.

Metal complexes of the constrained geometry type containing two metal centers joined by means of a dianionic ligand separate from and unconnected to the ligand groups in such complexes that contain delocalized 7-electrons, are previously taught, but not exemplified, in U.S. Pat. No. 5,055,438.

SUMMARY OF THE INVENTION

According to the present invention there is provided a composition comprising:

1) one or more bimetallic complexes corresponding to the formula:

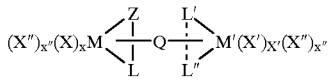

wherein:

M and M' are independently Group 3, 4, 5, 6, or Lanthanide metals;

L is a divalent group (or trivalent group if bound to Q) having up to 50 nonhydrogen atoms and containing an aromatic π-system through which the group is bound to M, said L also being bound to Z;

L' is a monovalent group or a divalent group (if bound to L" or Q), or a trivalent group (if bound to both L" and Q) having up to 50 nonhydrogen atoms and containing an aromatic π-system through which the group is bound to M';

L" is a monovalent group or a divalent group (if bound to L' or Q), or a trivalent group (if bound to both L' and Q) having up to 50 nonhydrogen atoms and containing an aromatic π-system through which the group is bound to M', or L" is a moiety comprising boron or a member of Group 14 of the Periodic Table of the Elements, and optionally also comprising nitrogen, phosphorus, sulfur or oxygen, said L" having up to 20 non-hydrogen atoms;

Z is a moiety comprising boron or a member of Group 14 of the Periodic Table of the Elements, and optionally also comprising nitrogen, phosphorus, sulfur or oxygen, said Z having up to 20 non-hydrogen atoms;

X and X' independently each occurrence are anionic ligand groups having up to 40 atoms exclusive of the class of ligands containing an aromatic or conjugated dienyl π-system through which the group is bound to M or M', or optionally two X groups or two X' groups together form a divalent, $C_{4-40}$ conjugated or nonconjugated dienyl ligand, optionally substituted with one or more hydrocarbyl, silyl, halocarbyl, or halohydrocarbyl groups, that together with M or M' form a metallocyclopentene moiety; or further optionally, two X groups or two X' groups together form a neutral, $C_{4-40}$ conjugated or nonconjugated diene ligand, optionally substituted with one or more hydrocarbyl, silyl, halocarbyl, or halohydrocarbyl groups, that is π-bonded to M or M' respectively.

X" independently each occurrence is a neutral ligating compound having up to 20 atoms, exclusive of neutral dienes;

Q is a divalent anionic ligand group bound at one terminus to either Z or L and bound at the remaining terminus to either L' or L", said Q having up to 20 nonhydrogen atoms; and x, x', and x" are independently integers from 0 to 3; and 2) one or more activating cocatalysts;

wherein activating cocatalyst component 2) causes both metal centers, e.g., M and M', of the one or more metal complexes 1) to possess at least partial ligand separation or to form an ion or zwitterion such that the composition is catalytically active for the polymerization of addition polymerizable monomers.

More preferably such poly-activated metal complexes are readily soluble in hydrocarbons thereby resulting in complexes having improved stability and longer catalyst lifetimes. Highly preferably, the metal complexes have at least one metal center that is doubly activated, so that two ligand groups thereof are at least partially separated from the metal or each metal forms a dication or a double zwitterion (doppelzwitterion). Most preferably, the poly-activated, bimetallic complex is formally tetracationic, that is, both metal centers thereof exist in the form of dications or double zwitterions (doppelzwitterions), e.g., the complex may be depicted as a tetracation or bis(doppelzwitterion).

Additionally according to the present invention there are provided polymerization catalysts comprising the foregoing poly-activated metal complexes, specially such complexes wherein one or both metal centers are double activated, the use thereof in addition polymerizations to prepare olefin polymers, and the resulting olefin polymers, particularly polymers having improved physical properties.

The invention allows for increased incidence of long chain branching in a polymer formed from a single monomer, especially ethylene, or a mixture of monomers. It is believed, without wishing to be bound by such belief, this is because a vinyl terminated polymer chain formed at one active metal polymerization site (for example due to β-hydride elimination in the growing polymer chain) has an increased probability of interaction with the adjoined metal center, thereby becoming incorporated into another polymer chain and resulting in the formation of long chain branched polymers. Thus, linking two catalyst centers effectively increases the probability of long chain branched polymer formation by increasing the number of catalytically active metal centers in the vicinity of the in situ formed vinyl terminated polymer. Alternatively, such catalyst compositions allow the artisan to attain increased long chain branching even under conditions that are not particularly conducive for such polymer formation, such as gas phase polymerization processes or solution polymerization processes operated at increased concentrations of ethylene or higher α-olefin. Accordingly, one beneficial result is the preparation of lower density ethylene/α-olefin copolymers (produced at higher α-olefin concentrations) that contain long chain branching or increased quantities of long chain branching. Examples of such polymers are ethylene/α-olefin copolymers, especially ethylene/1-butene-, ethylene/1-hexene- or ethylene/1-octene-copolymers having densities less than 0.895 g/ml, preferably less than 0.890 g/ml, and levels of long chain branching greater than 2 chains per 10,000 carbons, preferably greater than 3 chains per 10,000 carbons. Particularly beneficial properties are found in ethylene α-olefin copolymers according to the invention that are prepared by use of a continuous solution polymerization process, particularly one operating at relatively high ethylene conversion conditions.

The invented catalyst compositions also allow the preparation of mixtures of polymers or copolymers from a single monomer or mixture of monomers thereby forming directly a polymer blend in the reactor. This difference in properties among such polymers may be accentuated by using different metals, different metal valencies, different levels of activation, or different ligand groups attached to the two metal centers. Alternatively, the use of non-equivalent metal centers may be used to enhance long chain branching, where, for example, one metal center is adapted to forming oligomeric products terminated by vinyl functionality and the second metal center is adapted to form high molecular weight polymers or adapted to greater long chain α-olefin incorporation into a polymer.

The properties of polymers formed according to the invention are subject to variation and control by selection of the type of activator used in the catalyst composition. In particular, it is desirable to employ a relatively effective activating cocatalyst, particularly a non-polymeric, non-oligomeric, strong Lewis acid, in at least a 2:1 molar ratio with the metal complex, preferably at least a 3:1 molar ratio with the metal complex, and most preferably at least a 4:1 molar ratio with the metal complex, in order to simultaneously activate both metal centers of the dinuclear complex, and especially in order to doubly activate either or both metal centers. In general, activators or cocatalysts that operate by a charge transfer mechanism, especially by the principle of proton transfer, as well as alumoxanes or modified alumoxanes do not produce compositions having metal centers that are doubly activated.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups. Where referred to herein, the teachings of any publication, patent or patent application are hereby incorporated by reference herein. When a ligand group is stated as being monovalent, divalent or trivalent, respectively, it is meant that such ligand is connected to one, two or three further named ligands or elements in the illustrated formula, and does not indicate oxidation state or total ligand functionality. When a ligand is depicted as being bonded to a multiatomic group or bonded generically to a ring system, it is understood that the bond may be to any eligible atom of the multiatomic group or ring system.

As used herein the term "long chain branching" refers to pendant oligomeric, hydrocarbyl groups attached to a polymeric chain, which groups have a carbon length of six or greater, but are not the remnant of only a deliberately added α-olefin comonomer, e.g., 1-octene. Long chain branching in the present context includes polymer branches resulting from the reincorporation of vinyl-terminated polymer remnants resulting from β-hydride elimination. Accordingly, such long chain branches reflect the monomer diversity present in the polymerization reactor, since in effect, they are portions of previously formed polymer that are reincorporated into a growing polymer chain.

Several techniques may be used for measuring the extent of long chain branching in a copolymer. Principle analytical techniques include those based on $^{13}$C-NMR analysis, optionally coupled with low angle laser light scattering or similar particle size measuring technique to distinguish long chain and short chain branches and quantify the former. Additionally, it is possible to arrive at an estimate of short chain branches, i.e., branches due to the $C_{3-8}$ comonomer remnant, by preparation of a control copolymer using a labeled monomer, such as $^{13}$C-enriched 1-octene or ethylene, under the assumption that a similar level of branch distribution will exist in copolymers made under comparative conditions utilizing non-enriched monomer. The labeled short chains (using labeled 1-octene) may thereafter be directly measured by $^{13}$C NMR and the level of long chain branching as a portion of total branching thereafter determined by subtraction. Using labeled ethylene, any directly measured branches would presumably be due solely to long chain branch formation.

The presence of long chain branching is also qualitatively inferred from properties of the resulting polymer. Generally, the melt rheology of the polymer is significantly improved. That is, polymers having long chain branching have less resistance to flow under pressure without concomitant loss of melt strength. Particularly, desirable are copolymers having a melt flow ratio, I10/I2, greater than 5.63, preferably greater than 6.0, a molecular weight distribution, Mw/Mn, defined by the equation: Mw/Mn<(I10/I2)−4.63, and a critical shear stress at onset of gross melt fracture of greater than about $4 \times 10^6$ dynes/cm$^2$, preferably greater than $9 \times 10^6$ dynes/cm$^2$.

Preferred metal coordination complexes according to the present invention correspond to the following formula II:

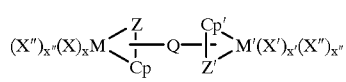
(II)

wherein Z, M, M', X, X', X", x, x', and x" are as previously defined;

Z' is a moiety comprising boron or a member of Group 14 of the Periodic Table of the Elements, and optionally also comprising nitrogen, phosphorus, sulfur or oxygen, said Z' having up to 20 non-hydrogen atoms;

Cp and Cp' are cyclic $C_5R'_4$ groups bound to Z or Z' respectively and bound to M or M' respectively by means of delocalized π-electrons, wherein R', independently each occurrence, is hydrogen, hydrocarbyl, silyl, halo, fluorohydrocarbyl, hydrocarbyloxy, hydrocarbylsiloxy, N,N-di(hydrocarbylsilyl)amino, N-hydrocarbyl-N-silylamino, N,N-di(hydrocarbyl) amino, hydrocarbyleneamino, di(hydrocarbyl) phosphino, hydrocarbylsulfido; or hydrocarbyloxy-substituted hydrocarbyl, said R' having up to 20 nonhydrogen atoms, and optionally, two such R' substituents may be joined together thereby causing Cp or Cp' to have a fused ring structure, or further optionally, Cp or Cp' each independently is a trivalent derivative of the above identified $C_5R'_4$ group that is also bonded to Q and one R' on each of Cp or Cp' is a covalent bond to Q;

Q is S, P, or a linear or cyclic hydrocarbylene or silanediyl group or nitrogen, oxygen, or halo substituted derivative thereof, said Q having up to 20 nonhydrogen atoms.

More preferred metal coordination complexes according to the present invention correspond to the following formula III:

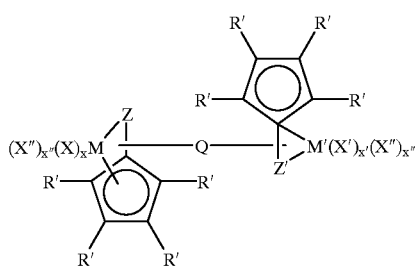
(III)

wherein:

M and M' independently each occurrence are Ti, Zr, Hf, Sc, yttrium, or La;

Q, X, X', X", x, x' and x" are as previously defined with respect to formula I;

R' each occurrence is hydrogen, hydrocarbyl, silyl, germyl, halo, cyano, halohydrocarbyl, hydrocarbyloxy, hydrocarbylsiloxy, di(hydrocarbylsilyl)amino, hydrocarbylsilylamino, di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two R' groups together form a divalent derivative thereof connected to adjacent positions of the cyclopentadienyl ring thereby forming a fused ring structure, or R' in one occurrence per cyclopentadienyl system is a covalent bond to Q;

Z and Z' independently each occurrence are —Z*Y'—, wherein:

Y' is —O—, —S—, —NR"—, —PR"—, —OR", or —NR"$_2$ (and with respect to —OR" and —NR"$_2$, one bond is a dative bond through the available electron pair), wherein R" is hydrogen, hydrocarbyl, silyl, or silylhydrocarbyl of up to 12 nonhydrogen atoms, or R" is a covalent bond to Q, and Z* is SiR*$_2$, CR*$_2$, SiR*$_2$SiR*$_2$, CR*$_2$CR*$_2$, CR*=CR*, CR*$_2$SiR*$_2$, or GeR*$_2$;

wherein R* each occurrence is independently hydrogen, hydrocarbyl, silyl, halogenated alkyl, or halogenated aryl, said R* having up to 12 non-hydrogen atoms.

More highly preferred metal coordination complexes are amidosilane- or amidoalkanediyl-compounds corresponding to the following formula (IV):

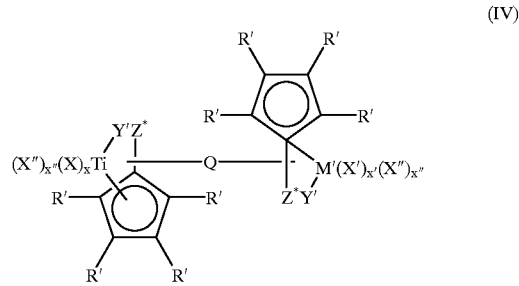
(IV)

wherein:

Q is a linear or cyclic hydrocarbylene, cyclohydrocarbylene or silanediyl group, or a nitrogen or oxygen containing derivative thereof, M' is Ti, Zr or Hf;

R' is as previously defined with respect to formula III;

X and X' are halide, $C_{1-10}$ hydrocarbyl, or di($C_{1-10}$ hydrocarbyl)amido; and Y'Z* is: —NR"—(ER'")$_m$— wherein:

E is independently each occurrence silicon or carbon;

R" is $C_{1-10}$ hydrocarbyl or a covalent bond to Q;

R'" is $C_{1-4}$ alkyl, phenyl, or a covalent bond to Q; and m is an integer from 1 to 10.

Preferably, R' independently each occurrence is hydrogen, hydrocarbyl, silyl, fluorophenyl, hydrocarbyloxy, N,N-di(hydrocarbyl)amino, hydrocarbyleneamino, or hydrocarbyloxy-substituted hydrocarbyl, said R' having up to 20 non-hydrogen atoms, or two adjacent R' groups are joined together forming part of a fused ring system. Most preferably, R' is hydrogen, methyl, ethyl, propyl, butyl, pentyl, hexyl, (including where appropriate all isomers), cyclopentyl, cyclohexyl, norbornyl, benzyl, phenyl, N,N-di (methyl)amino, pyrrolyl, pyrrolidinyl, piperidinyl, morpholinyl, or two R' groups are linked together, the entire $C_5R'_4$ group thereby forming an indenyl, tetrahydroindenyl, fluorenyl, tetrahydrofluorenyl, indacenyl, or octahydrofluorenyl group, or a $C_{1-6}$ hydrocarbyl-substituted, N,N-di(methyl)amino-, pyrrolidinyl-, or piperidinyl-substituted derivative thereof.

Examples of suitable X or X' groups for all of the foregoing structural depictions of the invention include single atomic groups including hydride or halide, as well as multi-atomic groups such as hydrocarbyl, hydrocarbyloxy, dihydrocarbylamido (including cyclic hydrocarbyleneamido groups) and halo, amino, or phosphino substituted derivatives thereof, said multi-atomic groups containing up to 20 nonhydrogen atoms. Specific examples include chloride, methyl, benzyl, allyl, N,N-dimethylamido, pyrrolinado, pyrrolidinado, (N,N-dimethylamino)benzyl, phenyl, methoxide, ethoxide, isopropoxide and isobutoxide. Most preferably X and X' are chloride, methyl, N,N-dimethylamido, or benzyl.

In the embodiments wherein two X or wherein two X' groups together form a diene group or substituted diene group, such group may form a π-complex with M or M' or the diene may form a σ-complex with M or M'. In such complexes M and M' are preferably Group 4 metals, most preferably Ti. In such complexes in which the diene is associated with the metal as a σ-complex, the metal is in the +4 formal oxidation state and the diene and metal together form a metallocyclopentene. In such complexes in which the diene is associated with the metal as a π-complex, the metal is in the +2 formal oxidation state, and the diene normally assumes a s-trans configuration or an s-cis configuration in which the bond lengths between the metal and the four carbon atoms of the conjugated diene are nearly equal. The dienes of complexes wherein the metal is in the +2 formal oxidation state are coordinated via π-complexation through the diene double bonds and not through a metallocycle resonance form containing σ-bonds. The nature of the bond is readily determined by X-ray crystallography or by NMR spectral characterization according to the techniques of Yasuda, et al., *Organometallics*, 1, 388 (1982), (Yasuda I); Yasuda, et al. *Acc. Chem. Res.*, 18, 120 (1985), (Yasuda II); Erker, et al., *Adv. Organomet. Chem.*, 24, 1 (1985)(Erker, et al. (I)); and U.S. Pat. No. 5,198,401. By the term "π-complex" is meant both the donation and back acceptance of electron density by the ligand are accomplished using ligand π-orbitals. Such dienes are referred to as being π-bound. It is to be understood that the present complexes may be formed and utilized as mixtures of the π-complexed and σ-complexed diene compounds.

The formation of the diene complex in either the π or σ state depends on the choice of the diene, the specific metal complex and the reaction conditions employed in the preparation of the complex. Generally, terminally substituted dienes favor formation of π-complexes and internally substituted dienes favor formation of σ-complexes. Especially useful dienes for such complexes are compounds that do not decompose under reaction conditions used to prepare the complexes of the invention. Under subsequent polymerization conditions, or in the formation of catalytic derivatives of the present complexes, the diene group may undergo chemical reactions or be replaced by another ligand.

Examples of suitable dienes (two X or X' groups taken together) include: butadiene, 1,3-pentadiene, 1,3-hexadiene, 2,4-hexadiene, 1,4-diphenyl-1,3-butadiene, 3-methyl-1,3-pentadiene, 1,4-dibenzyl-1,3-butadiene, 1,4-ditolyl-1,3-butadiene, and 1,4-bis(trimethylsilyl)-1,3-butadiene.

Examples of the preferred metal complexes according to the present invention include compounds wherein R'' is methyl, ethyl, propyl, butyl, pentyl, hexyl, (including all isomers of the foregoing where applicable), cyclododecyl, norbornyl, benzyl, phenyl, or a covalent bond to Q; Q is 1,6-hexanediyl or silanediyl, and the cyclic delocalized π-bonded group is cyclopentadienyl, tetramethylcyclopentadienyl, indenyl, tetrahydroindenyl, 2-methylindenyl, 2,3-dimethylindenyl, 2-methyl-4-phenylindenyl, 3-N,N-dimethylaminoindenyl, 3-(pyrrolidinyl)inden-1-yl, 3-(piperidinyl)inden-1-yl, fluorenyl, tetrahydrofluorenyl, indacenyl or octahydrofluorenyl group; M is titanium in the +2, +3 or +4 formal oxidation state; M' is scandium in the +3 formal oxidation state, titanium in the +2, +3 or +4 formal oxidation state, or zirconium in the +4 formal oxidation state.

Examples of the foregoing metal complexes include all of the following (where methyl groups are represented by line segments and ( )$_n$ indicates a $C_{1-20}$ hydrocarbylene bridging group):

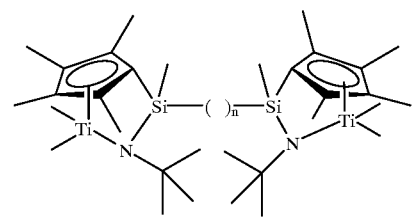

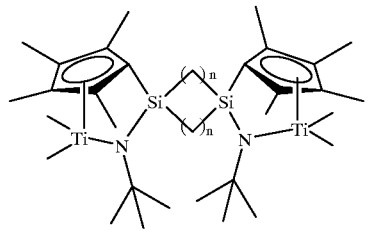

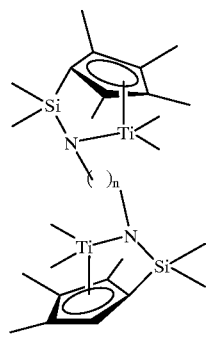

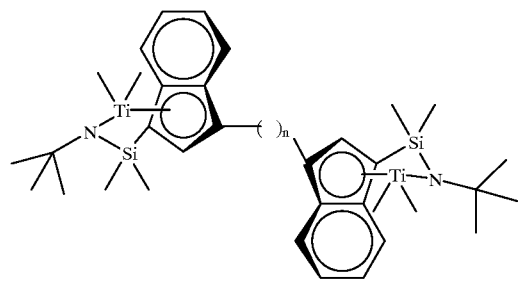

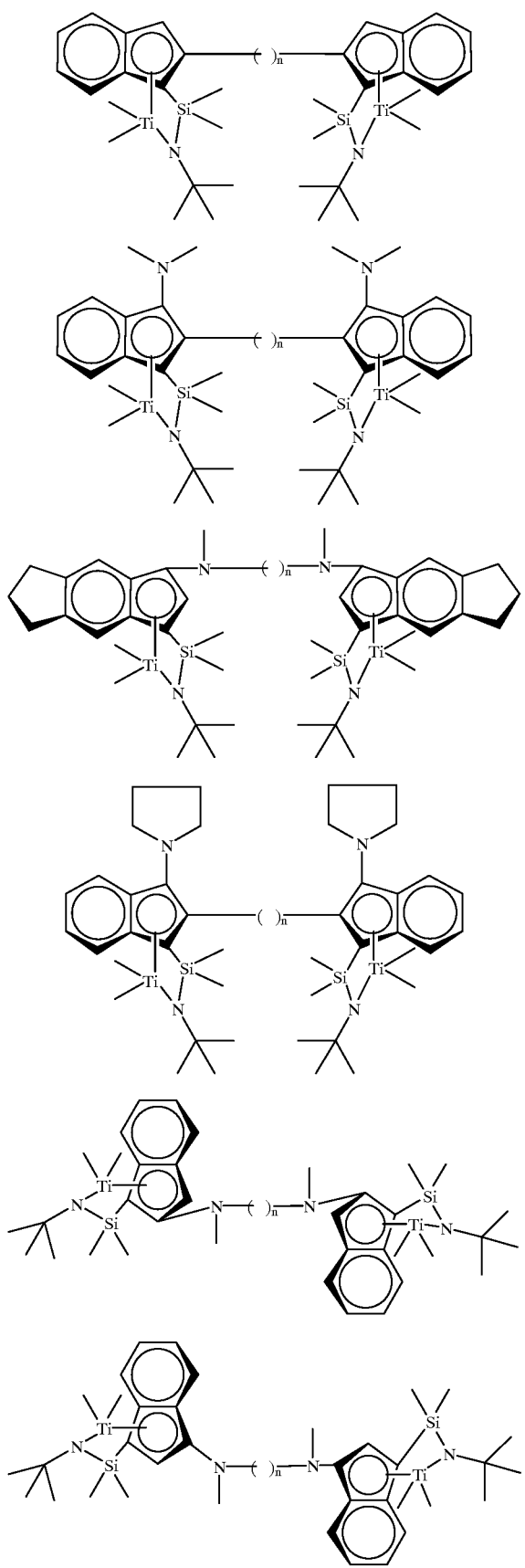

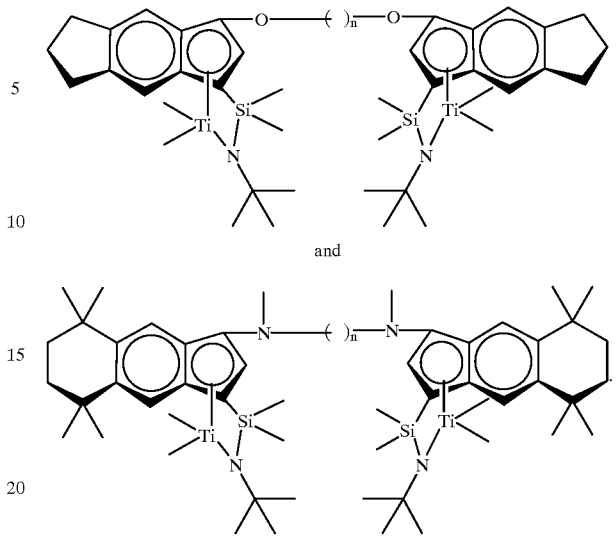

and

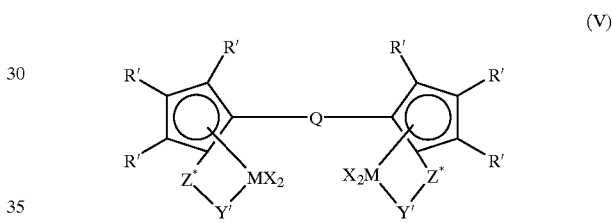

More preferred still according to the invention are zirconium and titanium bimaetallic complexes corresponding to the formula (V):

$$\text{(V)}$$

wherein:
M independently each occurrence is titanium or zirconium;
R' each occurrence is hydrogen, hydrocarbyl, silyl, germyl, halo, cyano, halohydrocarbyl, hydrocarbyloxy, hydrocarbylsiloxy, di(hydrocarbylsilyl)amino, hydrocarbylsilylamino, di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two R' groups together form a divalent derivative thereof connected to adjacent positions of the cyclopentadienyl ring thereby forming a fused ring structure,
Z*—Y' is as previously defined with respect to formula III; and
X independently each occurrence is an anionic ligand group having up to 40 atoms exclusive of the class of ligands containing an aromatic π-system through which the group is bound to M, or optionally two X groups together form a $C_{4-40}$ conjugated or nonconjugated diene optionally substituted with one or more hydrocarbyl, silyl, halocarbyl, or halohydrocarbyl groups; and
Q is a divalent anionic ligand group having up to 20 nonhydrogen atoms.

Especially preferred metal coordination complexes correspond to the foregoing formula V, wherein
Q is a linear or cyclic hydrocarbylene or silane group of up to 20 atoms other than hydrogen;

R' is hydrogen, $C_{1-20}$ hydrocarbyl, or two adjacent R' groups are joined together forming part of a fused ring system;

X is chloride, iodide, $NR''_2$, or R''; wherein R'' is $C_{1-10}$ hydrocarbyl; and Y'Z is: $-NR''-(ER''')_m-$ wherein:

E is independently each occurrence silicon or carbon;

R'' is $C_{1-10}$ hydrocarbyl;

R''' is $C_{1-4}$ alkyl; and m is an integer from 1 to 10.

Even more further preferred metal coordination complexes according to the present invention correspond to the foregoing formula VI, wherein M in both occurrences is titanium or zirconium;

Q is $C_{4-12}$ hydrocarbylene, preferably 1,6-hexanediyl;

the unsaturated ring system is cyclopentadienyl or indenyl;

X is chloride, iodide, N,N-dimethylamido, benzyl or methyl; and

Y'Z is: dimethyl(t-butylamido)silanediyl.

Such complexes are of the formula VI, or an etherate derivative thereof:

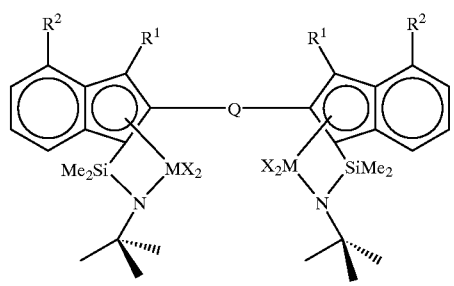

(VI)

wherein M is titanium or zirconium, Q is $C_{4-12}$ hydrocarbylene, X is methyl or dimethylamido, and $R^1$ and $R^2$ are both hydrogen, $R^1$ is methyl and $R^2$ is phenyl, or $R^1$ is pyrrolidinyl and $R^2$ is hydrogen.

Other preferred metal complexes are silane bridged complexes of formula VII, where M, M', X, X', x, x', R', Y' Z*, and Q are as defined for formula IV:

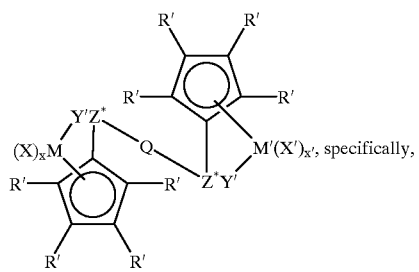

(VII)

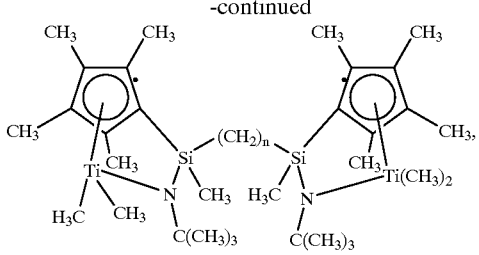

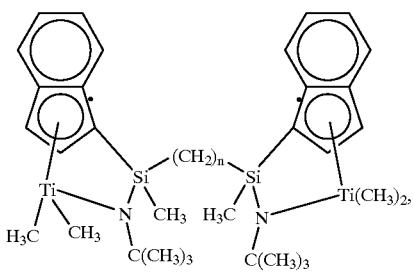

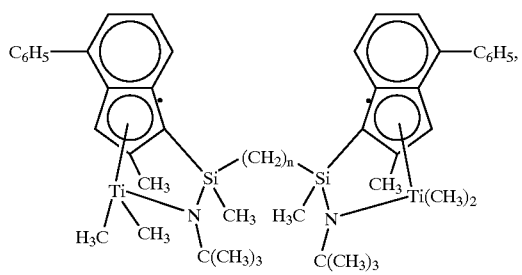

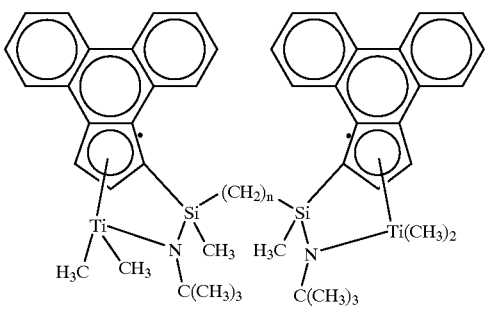

or

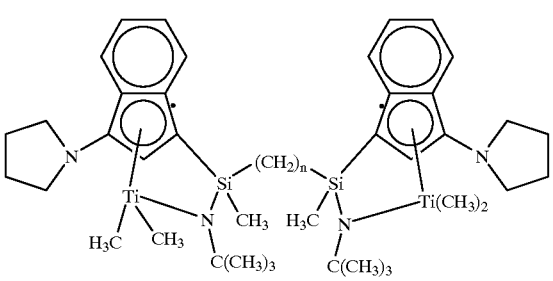

and n is an integer from 4 to 12;

or amido-bridged complexes of the formula VIII, where M, M', X, X', x, x', R', Y' Z*, and Q are as defined for formula IV:

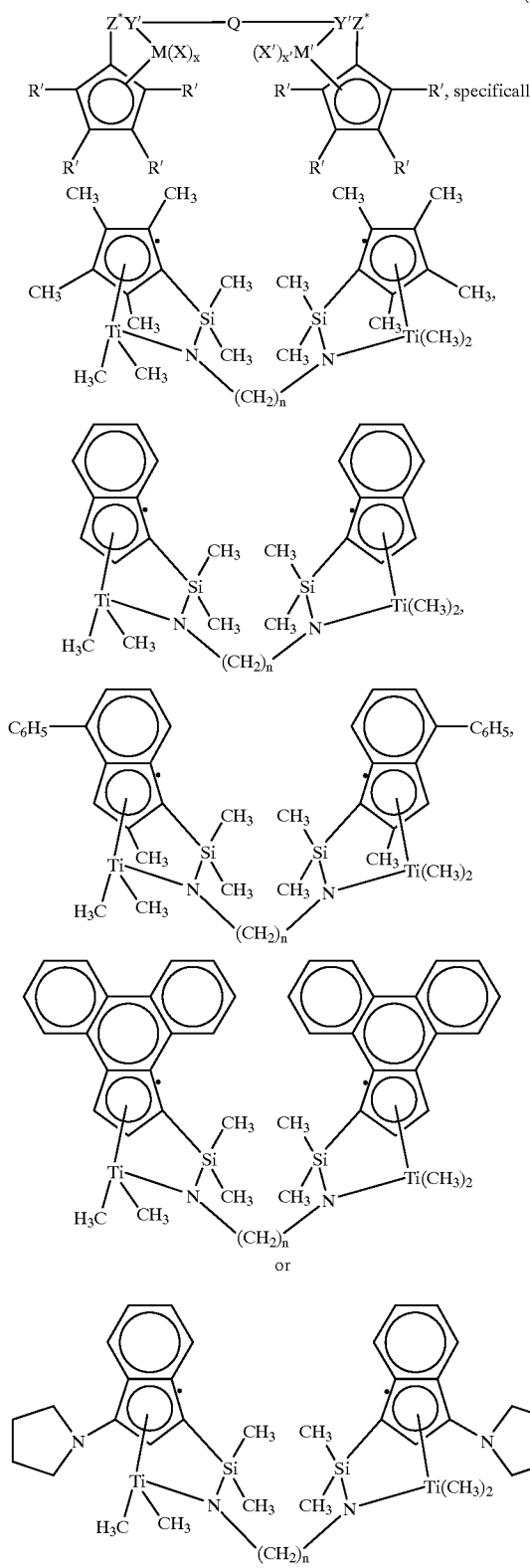

and n is an integer from 4 to 20.

Most highly preferred bimetallic complexes for use according to the present invention include: zirconium, di(N, N-dimethylamido)(N-(1,1-dimethylethyl)-1-((1,2,3,3a,7a-η)-1H-inden-1-yl)-1,1-dimethylsilanaminato(2-)-N)(3,3'-(1, 6-hexanediyl)bis-, zirconium, dimethyl(N-(1,1-dimethylethyl)-1-((1,2,3,3a,7a-η)-1H-inden-1-yl)-1,1-dimethylsilanaminato(2-)-N)(3,3'-(1,6-hexanediyl)bis-, titanium, di(N,N-dimethylamido)(N-(1,1-dimethylethyl)-1-((1,2,3,3a,7a-η)-1H-inden-1-yl)- 1,1-dimethylsilanaminato (2-)-N)(3,3'-(1,6-hexanediyl)bis-, and titanium, dimethyl(N-(1,1-dimethylethyl)-1-((1,2,3,3a,7a-η)-1H-inden-1-yl)-1,1-dimethylsilanaminato(2-)-N)(3,3'-(1,6-hexanediyl)bis-, {(methyl)(hexan-1,6-diyl)silyl-N-(t-butyl)(tetramethylcyclopentadienyl)-titanium diiodide}bis-, In general, the complexes of the present invention can be prepared using standard techniques of organic or organo-metallic synthesis using a suitable noninterfering solvent at a temperature from −100° C. to 300° C., preferably from −78 to 130° C., most preferably from −10 to 120° C. More particularly, the complexes can be prepared by reacting a compound of the formula: HL—Z—Q—L'—L"H (where L, Z, Q, L', and L" are as defined in formula 1) such as 1,6-hexane (bisinden-1-yl)methylchlorosilane) with 4 equivalents of an amine, preferably t-butylamine, and then tetrametallating reacting the resulting product with a metal halide, such as titanium or zirconium tetrachloride, titanium trichloride, titanium dichloride, zirconium dichloride, or a Lewis base adduct thereof, and optionally oxidizing the resulting metal complex. The corresponding hydrocarbyl or diene derivative may be prepared by known exchange of the halide complex with the metal hydrocarbyl or conjugated diene, optionally under reducing conditions. Alternatively, the desired bimetal dihydrocarbyl complex can be directly formed by reaction with a titanium or zirconium tetraamide, especially titanium tetra(N,N-dimethylamide) or zirconium tetra(N,N-dimethylamide), under ring formation conditions, followed by reaction with excess aluminum trialkyl to form the desired tetraalkyl derivative. Alternatively, the desired bimetal dihyrdrocarbyl complex can be directly formed under ring forming conditions by reaction of the ligand with a titanium or zirconium tetralkyl, especially titanium tetrakis (benzyl) and zirconium tetrakis(benzyl). Modifications of the foregoing preparation procedures to prepare alternative compounds of the invention may be employed by the skilled artisan without departing from the scope of the present invention.

Suitable reaction media for the formation of the complexes are aliphatic and aromatic hydrocarbons and halohydrocarbons, ethers, and cyclic ethers. Examples include straight and branched-chain hydrocarbons such as $C_{4-12}$ alkanes and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, xylene, and $C_{1-4}$ dialkyl ethers, $C_{1-4}$ dialkyl ether derivatives of (poly) alkylene glycols, and tetrahydrofuran. Mixtures of the foregoing list of suitable solvents are also suitable.

The recovery procedure involves separation of the resulting alkali metal or alkaline earth metal salt and devolatilization of the reaction medium. Extraction into a secondary solvent may be employed if desired. Alternatively, if the desired product is an insoluble precipitate, filtration or other separation technique may be employed.

A preferred method of preparing the complexes employed in the present catalyst composition is according to the following schematic reaction:

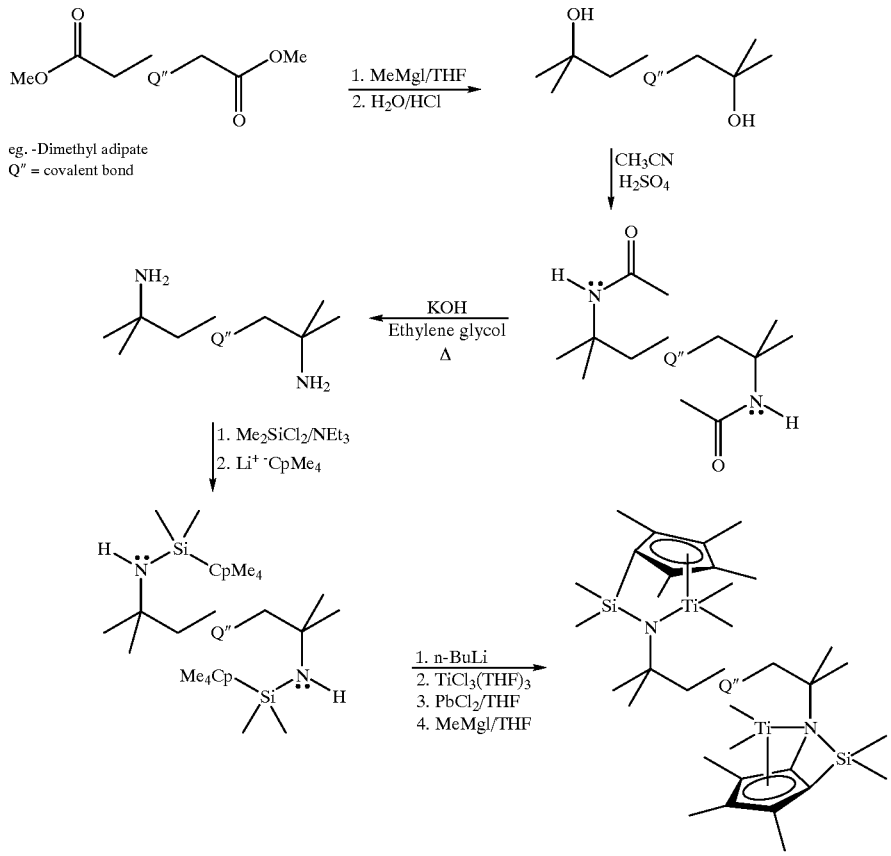

The dihydrocarbyl complexes can be further purified by reaction with iodine to give the tetraiodo bimetal complexes. The purified tetraiodo complexes can be alkylated with metal hydrocarbyl reagents, preferably methyl magnesium iodide, to give the tetrahydrocarbyl complexes in high yield and purity.

Further preferably, the metal complexes contain a relatively large aliphatic or cycloaliphatic bridging group, Q. Most preferably, such Q groups are $C_{5-20}$ alkylene or cycloalkylene. Such complexes are more soluble in hydrocarbons or deuterated hydrocarbons and the activated catalysts formed therefrom have longer lifetimes than those of metal complexes having less hydrophilic Q bridging groups. Most preferably the activated metal complexes have half lives in benzene-$d_6$ or toluene-$d_8$ at 25° C., as measured by NMR spectroscopy, of 5 minutes or greater, preferably 10 minutes or greater, most preferably 30 minutes or greater. Alternatively, the metal complexes can be rendered more soluble, and the activated derivatives more stable, by use of more polar solvents, such as diethyl ether. In addition, where the Q group is bonded to a cyclopentadienyl group, it is preferably bonded at the 2-position, as in complexes of formula V or VI.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or diisobutylalumoxane; strong Lewis acids, especially $C_{1-30}$ hydrocarbyl) substituted Group 13 compounds, especially tri(hydrocarbyl)aluminum-, tri(hydrocarbyl)boron compounds, halogenated derivatives thereof, having from 1 to 10 carbons in each hydrocarbyl or halogenated hydrocarbyl group, and mixtures thereof. Especially preferred are perfluorinated tri(aryl)aluminum- or perfluorinated tri(aryl)boron-compounds, or mixtures thereof, and most especially tris(pentafluorophenyl)aluminum, 1,4-tetrafluorophenylene bis{bis(pentafluorophenyl)aluminum}, tris(pentafluorophenyl)boron, 1,4-tetrafluorophenylene bis{bis(pentafluorophenyl)boron}, and mixtures thereof. Also suitable are nonpolymeric, ionic, compatible, noncoordinating, activating compounds (including the use of such compounds under oxidizing conditions); and combinations of all of the foregoing.

Suitable activating compounds useful as a cocatalyst in one embodiment of the present invention comprise a cation which is a Bronsted acid capable of donating a proton, and an inert, compatible, noncoordinating, anion, $A^-$. Preferred anions are those containing a single coordination complex comprising a charge-bearing metal or metalloid core which anion is capable of balancing the charge of the active catalyst species (the metal cation) which is formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially. Therefore, said single boron atom compounds are preferred.

Preferably such cocatalysts may be represented by the following general formula:

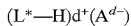

wherein:
L* is a neutral Lewis base;
(L*—H)$^+$ is a Bronsted acid;
A$^{d-}$ is a noncoordinating, compatible anion having a charge of d–, and
d is an integer from 1 to 3.

More preferably A$^{d-}$ corresponds to the formula:

wherein:
k is an integer from 1 to 3;
n' is an integer from 2 to 6;
n'-k=d;
M' is an element selected from Group 13 of the Periodic Table of the Elements; and
Q' independently each occurrence is an hydride, dialkylamido, halide, alkoxide, aryloxide, hydrocarbyl, or halosubstituted-hydrocarbyl radical, said Q' having up to 20 carbons with the proviso that in not more than one occurrence is Q' halide.

In a more preferred embodiment, d is one, that is, the counter ion has a single negative charge and corresponds to the formula A$^-$. Activating cocatalysts comprising boron which are particularly useful in the preparation of catalysts of this invention may be represented by the following general formula:

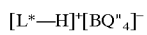

wherein:
L* is as previously defined;
B is boron in a valence state of 3; and
Q" is a fluorinated C$_{1-20}$ hydrocarbyl group.

Most preferably, Q" is in each occurrence a fluorinated aryl group, especially a pentafluorophenyl group.

Illustrative, but not limiting examples of boron compounds which may be used as an activating cocatalyst in the preparation of the improved catalysts of this invention are tri-substituted ammonium salts such as:

trimethylammonium tetrakis(pentafluorophenyl)borate,
dimethylanilinium tetrakis(pentafluorophenyl)borate,
dimethyltetradecylammonium tetrakis(pentafluorophenyl)borate,
dimethyhexadecylammonium tetrakis(pentafluorophenyl)borate,
dimethyloctadecylammonium tetrakis(pentafluorophenyl)borate,
methylbis(tetradecyl)ammonium tetrakis(pentafluorophenyl)borate,
methylbis(hexadecyl)ammonium tetrakis(pentafluorophenyl)borate,
methylbis(octadecyl)ammonium tetrakis(pentafluorophenyl)borate, and mixtures thereof.

Another suitable ion forming, activating cocatalyst comprises a salt of a cationic oxidizing agent and a noncoordinating, compatible anion represented by the formula:

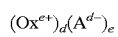

wherein:
Ox$^{e+}$ is a cationic oxidizing agent having a charge of e+;
e is an integer from 1 to 3; and
A$^{d-}$, and d are as previously defined.

Examples of cationic oxidizing agents include: ferrocenium, hydrocarbyl-substituted ferrocenium, Ag$^+$, or Pb$^{+2}$. Preferred embodiments of A$^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

wherein:
©$^+$ is a C$_{1-20}$ carbenium ion; and
A$^-$ is as previously defined. A preferred carbenium ion is the trityl cation, that is triphenylcarbenium.

A further suitable ion forming, activating cocatalyst comprises a compound which is a salt of a silylium ion and a noncoordinating, compatible anion represented by the formula: R$_3$Si(X')$_q^+$A$^-$, wherein:
R is C$_{1-10}$ hydrocarbyl, and X', q and A$^-$ are as previously defined.

Preferred silylium salt activating cocatalysts are trimethylsilylium tetrakis(pentafluorophenyl)borate, triethylsilylium tetrakis(pentafluorophenyl)borate and ether substituted adducts thereof. The use of the above silylium salts as activating cocatalysts for addition polymerization catalysts is known in the art, having been disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

Another class of suitable catalyst activators are expanded anionic compounds corresponding to the formula: (A$^{1+a1}$)$_{b^1}$ (Z$^1$J$^1$$_{j^1}$)$^{-c1}$$_{d^1}$, wherein
A$^1$ is a cation of charge +a$^1$,
Z' is an anion group of from 1 to 50, preferably 1 to 30 atoms, not counting hydrogen atoms, further containing two or more Lewis base sites;
J$^1$ independently each occurrence is a Lewis acid coordinated to at least one Lewis base site of Z$^1$, and optionally two or more such J$^1$ groups may be joined together in a moiety having multiple Lewis acidic functionality,
j$^1$ is a number from 2 to 12, and
a$^1$, b$^1$, c$^1$, and d$^1$ are integers from 1 to 3, with the proviso that a$^1$×b$^1$ is equal to c$^1$×d$^1$.

The foregoing cocatalysts (illustrated by those having imidazolide, substituted imidazolide, imidazolinide, substituted imidazolinide, benzimidazolide, or substituted benzimidazolide anions) may be depicted schematically as follows:

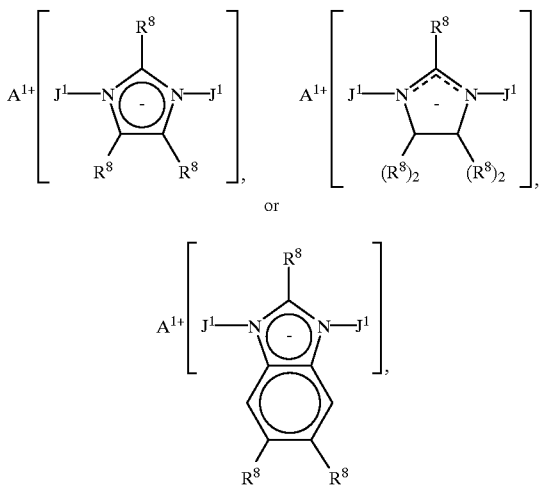

or

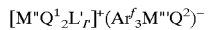

wherein:

A$^{1+}$ is a monovalent cation as previously defined, and preferably is a trihydrocarbyl ammonium cation, containing one or two C$_{10-40}$ alkyl groups, especially the methylbis(tetradecyl)ammonium- or methylbis(octadecyl)ammonium-cation, R$^8$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably C$_{1-20}$ alkyl, and J$^1$ is tris(pentafluorophenyl)boron or tris(pentafluorophenyl)aluminum.

Examples include the trihydrocarbylammonium-, especially, methylbis(tetradecyl)ammonium- or methylbis(octadecyl)ammonium-salts of:

bis(tris(pentafluorophenyl)borane)imidazolide,
bis(tris(pentafluorophenyl)borane)-2-undecylimidazolide,
bis(tris(pentafluorophenyl)borane)-2-heptadecylimidazolide,
bis(tris(pentafluorophenyl)borane)-4,5-bis(undecyl)imidazolide,
bis(tris(pentafluorophenyl)borane)-4,5-bis(heptadecyl)imidazolide,
bis(tris(pentafluorophenyl)borane)imidazolinide,
bis(tris(pentafluorophenyl)borane)-2-undecylimidazolinide,
bis(tris(pentafluorophenyl)borane)-4,5-bis(undecyl)imidazolinide,
bis(tris(pentafluorophenyl)borane)-4,5-bis(heptadecyl)imidazolinide,
bis(tris(pentafluorophenyl)borane)-5,6-dimethylbenzimidazolide,
bis(tris(pentaf luorophenyl)borane)-5,6-bis(undecyl)benzimidazolide,
bis(tris(pentafluorophenyl)alumane)imidazolide,
bis(tris(pentafluorophenyl)alumane)-2-undecylimidazolide,
bis(tris(pentafluorophenyl)alumane)-2-heptadecylimidazolide,
bis(tris(pentafluorophenyl)alumane)-4,5-bis(undecyl)imidazolide,
bis(tris(pentafluorophenyl)alumane)-4,5-bis(heptadecyl)imidazolide,
bis(tris(pentafluorophenyl)alumane)imidazolinide,
bis(tris(pentafluorophenyl)alumane)-2-undecylimidazolinide,
bis(tris(pentafluorophenyl)alumane)-4,5-bis(undecyl)imidazolinide,
bis(tris(pentafluorophenyl)alumane)-4,5-bis(heptadecyl)imidazolinide,
bis(tris(pentafluorophenyl)alumane)-5,6-dimethylbenzimidazolide, and
bis(tris(pentafluorophenyl)alumane)-5,6-bis(undecyl)benzimidazolide.

The foregoing activators are disclosed and claimed in U.S. Ser. No. 09/251,664, filed Feb. 17, 1999.

A further class of suitable activating cocatalysts include cationic Group 13 salts corresponding to the formula:

$$[M''Q^1_2L'_{l'}]^+(Ar^f_3M''Q^2)^-$$

wherein:

M'' is aluminum, gallium, or indium;

M''' is boron or aluminum;

Q$^1$ is C$_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more Q$^1$ groups may be covalently linked with each other to form one or more fused rings or ring systems;

Q$^2$ is an alkyl group, optionally substituted with one or more cycloalkyl or aryl groups, said Q$^2$ having from 1 to 30 carbons;

L' is a monodentate or polydentate Lewis base, preferably L' is reversibly coordinated to the metal complex such that it may be displaced by an olefin monomer, more preferably L' is a monodentate Lewis base;

l' is a number greater than zero indicating the number of Lewis base moieties, L', and Ar$^f$ independently each occurrence is an anionic ligand group; preferably Ar$^f$ is selected from the group consisting of halide, C$_{1-20}$ halohydrocarbyl, and Q$^1$ ligand groups, more preferably Ar$^f$ is a fluorinated hydrocarbyl moiety of from 1 to 30 carbon atoms, most preferably Ar$^f$ is a fluorinated aromatic hydrocarbyl moiety of from 6 to 30 carbon atoms, and most highly preferably Ar$^f$ is a perfluorinated aromatic hydrocarbyl moiety of from 6 to 30 carbon atoms.

Examples of the foregoing Group 13 metal salts are alumicinium tris(fluoroaryl)borates or gallicinium tris (fluoroaryl)borates corresponding to the formula: $[M''Q^1_2L'_{l'}]^+(Ar^f_3BQ^2)^-$, wherein M'' is aluminum or gallium; Q$^1$ is C$_{1-20}$ hydrocarbyl, preferably C$_{1-8}$ alkyl; Ar$^f$ is perfluoroaryl, preferably pentafluorophenyl; and Q$^2$ is C$_{1-8}$ alkyl, preferably C$_{1-8}$ alkyl. More preferably, Q$^1$ and Q$^2$ are identical C$_{1-8}$ alkyl groups, most preferably, methyl, ethyl or octyl. The foregoing activators are disclosed and claimed in U.S. Ser. No. 09/289,335, filed Apr. 9, 1999.

The foregoing activating technique and ion forming cocatalysts are also preferably used in combination with a tri(hydrocarbyl)aluminum compound having from 1 to 4 carbons in each hydrocarbyl group, an oligomeric or polymeric alumoxane compound, or a mixture of a tri(hydrocarbyl)aluminum compound having from 1 to 4 carbons in each hydrocarbyl group and a polymeric or oligomeric alumoxane.

When using an alumoxane cocatalyst the molar ratio of catalyst/cocatalyst employed preferably ranges from 1:10,000 to 100:1, more preferably from 1:5000 to 10:1, most preferably from 1:1000 to 1:1. Non-polymeric, strong Lewis acid- and Bronsted acid-activators are preferably used in molar ratios of catalyst/cocatalyst from 2:1 to 6:1, preferably from 4:1 to 5:1. In a particularly preferred embodiment of the invention these cocatalysts can be used in combination with a adjuvant that is a $C_{3-30}$ trihydrocarbyl aluminum compound, $C_{3-30}$ (hydrocarbyloxy)dihydrocarbyl aluminum compound, or an oligomeric or polymeric alumoxane, which adjuvants are employed for their beneficial ability to scavenge impurities such as oxygen, water, and aldehydes from the polymerization mixture. Preferred adjuvants for this application include $C_{2-6}$ trialkyl aluminum compounds, especially those wherein the alkyl groups are ethyl, propyl, isopropyl, n-butyl, isobutyl, pentyl, neopentyl, or isopentyl, and methylalumoxane, modified methylalumoxane and diisobutyl-alumoxane. The molar ratio of aluminum compound to metal complex is preferably from 1:10,000 to 1000:1, more preferably from 1:5000 to 100:1, most preferably from 1:100 to 100:1.

The poly-activated catalysts may exist as cationic derivatives of the dual metal center complexes, as zwitterionic derivatives thereof, or in an as yet undetermined relationship with the cocatalyst activator. In particular, those poly-activated catalysts resulting from use of a strong Lewis acid activator are believed to exist as dicationic (doppelzwitterionic) or tetracationic (bisdoppelzwitterionic) complexes. In general, the Bronsted acid cocatalysts and alumoxanes cocatalysts are believed to be incapable of doubly activating a metal center. A most highly preferred cocatalyst is trispentafluorophenylboron, trispentafluorophenylaluminum, mixtures thereof, and further mixtures of either or both Lewis acids with tri($C_{1-4}$) alkyl aluminum compounds.

In view of the foregoing, the resultant poly-activated metal complexes are believed to correspond to the following formula IA:

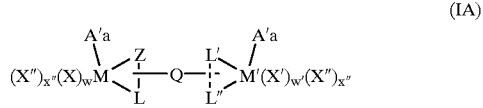

(IA)

wherein:
M and M' are independently Group 3, 4, 5, 6, or Lanthanide metals;
L is a divalent group (or trivalent group if bound to Q) having up to 50 nonhydrogen atoms and containing an aromatic π-system through which the group is bound to M, said L also being bound to Z;
L' is a monovalent group or a divalent group (if bound to L" or Q), or a trivalent group (if bound to both L" and Q) having up to 50 nonhydrogen atoms and containing an aromatic π-system through which the group is bound to M';
L" is a monovalent group or a divalent group (if bound to L' or Q), or a trivalent group (if bound to both L' and Q) having up to 50 nonhydrogen atoms and containing an aromatic π-system through which the group is bound to M', or L" is a moiety comprising boron or a member of Group 14 of the Periodic Table of the Elements, and optionally also comprising nitrogen, phosphorus, sulfur or oxygen, said L" having up to 20 non-hydrogen atoms;
Z is a moiety comprising boron or a member of Group 14 of the Periodic Table of the Elements, and optionally also comprising nitrogen, phosphorus, sulfur or oxygen, said Z having up to 20 non-hydrogen atoms;

X and X' independently each occurrence are anionic ligand groups having up to 40 atoms exclusive of the class of ligands containing an aromatic or conjugated dienyl π-system through which the group is bound to M or M', or optionally two X groups or two X' groups together form a divalent, $C_{4-40}$ conjugated or nonconjugated dienyl ligand, optionally substituted with one or more hydrocarbyl, silyl, halocarbyl, or halohydrocarbyl groups, that together with M or M' form a metallocyclopentene moiety; or further optionally, two X groups or two X' groups together form a neutral, $C_{4-40}$ conjugated or nonconjugated diene ligand, optionally substituted with one or more hydrocarbyl, silyl, halocarbyl, or halohydrocarbyl groups, that is π-bonded to M or M' respectively.

X" independently each occurrence is a neutral ligating compound having up to 20 atoms, exclusive of neutral dienes;

Q is a divalent anionic ligand group bound at one terminus to either Z or L and bound at the remaining terminus to either L' or L", said Q having up to 20 nonhydrogen atoms; and w, w', are independently integers from 0 to 2 selected to provide charge neutrality, x" is an integer from 0 to 3;

A' independently each occurrence is the remnant of the cocatalyst component causing the complex to possess complete or partial charge separation at each metal center; and a, independently each occurrence, is 1 or 2.

Preferably, the foregoing poly-activated metal complexes are those of the foregoing formula IA, wherein M and M' are independently Ti, Zr or Hf, preferably Ti, X and X' are $C_{1-20}$ hydrocarbyl, preferably methyl, a each occurrence is 1, and A' each occurrence is (μ-methyl)Al⁻($C_6F_5$)$_3$, (μ-Me)B⁻($C_6F_5$)$_3$, [B($C_6F_5$)$_4$]⁻, bis(tris(pentafluorophenyl)-alumane)-2-undecylimidazolinide, or bis(tris(pentafluorophenyl)borane)-2-undecylimidazolinide; or those of the foregoing formula IA, wherein M and M' are independently Ti, Zr or Hf, preferably Ti, X and X' are $C_{1-20}$ hydrocarbyl, preferably methyl, a in one occurrence is 2 and in the other occurrence is 1 or 2, antd A' each occurrence is (μ-methyl)Al⁻($C_6F_5$)$_3$.

Preferred poly-activated complexes of the invention are those derived from the foregoing metal complexes II, III or IV, namely those believed to have the following formulas:

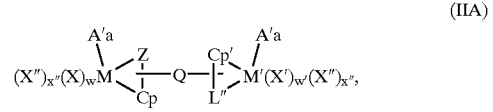

(IIA)

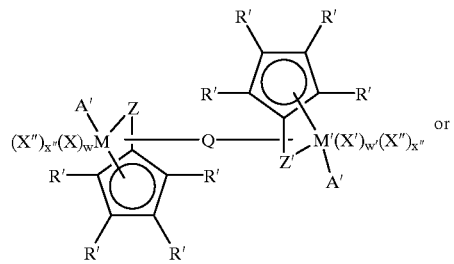

(IIIA)

or

-continued

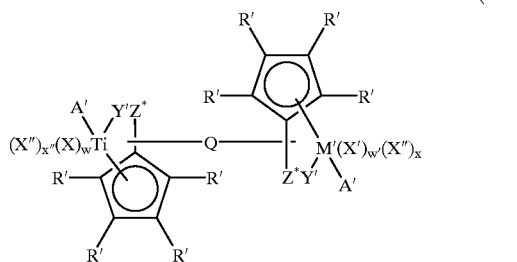
(IVA)

wherein all variables are as previously defined for formulas II, III, IV and IA respectively, including the preferred and most preferred embodiments thereof.

Specific examples of the most highly preferred polyactivated metal complexes correspond to the following structures:

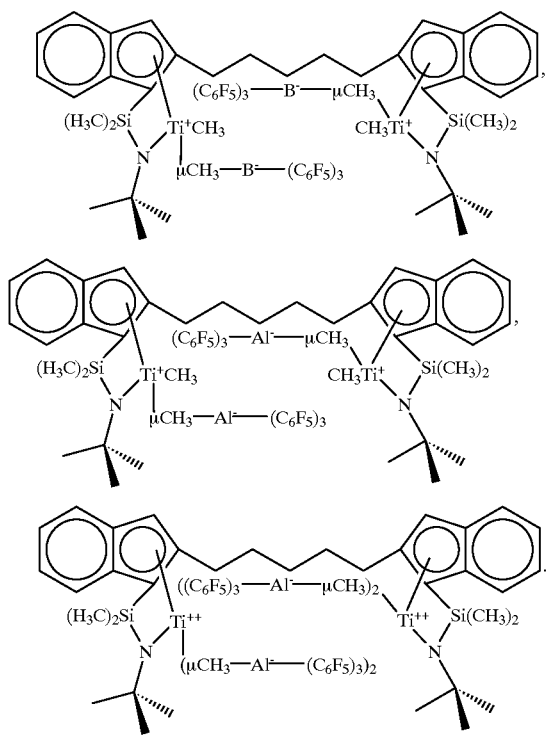

The catalysts may be used to polymerize ethylenically and/or acetylenically unsaturated monomers having from 2 to 20 carbon atoms either alone or in combination. Preferred monomers include the $C_{2-10}$ α-olefins especially ethylene, propylene, isobutylene, 1-butene, 1-hexene, 4-methyl-1-pentene, and 1-octene and mixtures thereof. Other preferred monomers include vinylcyclohexene, vinylcyclohexane, styrene, $C_{1-4}$ alkyl substituted styrene, tetrafluoroethylene, vinylbenzocyclobutane, ethylidenenorbornene and 1,4-hexadiene.

In general, the polymerization may be accomplished at conditions well known in the prior art for Ziegler-Natta or Kaminsky-Sinn type polymerization reactions, that is, temperatures from 0–250° C. and pressures from atmospheric to 3000 atmospheres. Suspension, solution, slurry, gas phase or high pressure, whether employed in batch or continuous form or under other process conditions, may be employed if desired. For example, the use of condensation in a gas phase polymerization is a especially desirable mode of operation for use of the present catalysts. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere, which teachings disclose conditions that can be employed with the polymerization catalysts of the present invention. A support, especially silica, alumina, or a polymer (especially polytetrafluoroethylene or a polyolefin) may be employed, and desirably is employed when the catalysts are used in a gas phase polymerization process with or without condensation. Methods for the preparation of supported catalysts are disclosed in numerous references, examples of which are U.S. Pat. Nos. 4,808,561, 4,912,075, 5,008,228, 4,914,253, and 5,086,025 and are suitable for the preparation of supported catalysts of the present invention.

In most polymerization reactions the molar ratio of catalyst:polymerizable compounds employed is from $10^{-12}$:1 to $10^{-1}$:1, more preferably from $10^{-12}$:1 to $10^{-5}$:1.

Suitable solvents for solution, suspension, slurry or high pressure polymerization processes are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene. Suitable solvents also include liquid olefins which may act as monomers or comonomers including ethylene, propylene, butadiene, cyclopentene, 1-hexene, 3-methyl-1-pentene, 4-methyl-1-pentene, 1,4-hexadiene, 1-octene, 1-decene, styrene, divinylbenzene, allylbenzene, and vinyltoluene (including all isomers alone or in admixture). Mixtures of the foregoing are also suitable.

Having described the invention the following examples are provided as further illustration thereof and are not to be construed as limiting. Unless stated to the contrary all parts and percentages are expressed on a weight basis. The invention herein disclosed may be performed in the absence of any reagent not specifically described. The term "overnight", if used, refers to a time of approximately 16–18 hours, "room temperature", if used, refers to a temperature of about 20–25° C., and "mixed alkanes" or "alkanes" refers to a mixture of mostly $C_6$–$C_{12}$ isoalkanes available commercially under the trademark Isopar E™ from Exxon Chemicals Inc.

All manipulations of air sensitive materials were performed in an argon filled, vacuum atmospheres, glove box or on a high vacuum line using standard Shlenk techniques. 1-N-pyrrolidineindene was prepared via the route of Noland, et al., JOC, 1981, 46, (1940). Its lithium salt, (1-(1-pyrrolidinyl)-1H-indenyl)lithium, was prepared by reaction with butyllithium in hexanes and recovered by filtration. Tris(perfluorophenyl)borane $(C_6F_5)_3B$ (FAB) was purchased as a solid from Boulder Scientific Inc. and further purified by recrystallization from hexane. Tris (perfluorophenyl)aluminum $(C_6F_5)_3Al$ (FAAL, as a toluene adduct or solvate free FAAL) was prepared by exchange reaction between tris(perfluorophenyl) borane and trimethylaluminum, substantially as reported by Biagini et. al., U.S. Pat. No. 5,602,269. All other reagents were purchased from commercial sources and used as received. Solvents were purified using the technique disclosed by Pangbom et al, Organometallics, 15, 1518–1520, (1996) or by passage through columns packed with activated alumina (Kaiser A-2) and supported copper (Engelhard, Cu-0224 S). $^1H$ and $^{13}C\{^1H\}$ NMR spectra are reported relative to tetramethylsilane and are referenced to the residual solvent peak. All chemical shifts for $^{19}F$ NMR spectra were relative to a fixed external standard (CFCl$_3$) in benzene-d$_6$ or toluene-d$_8$, both of which were dried over Na/K alloy and filtered or distilled prior to use.

EXAMPLE 1

Titanium, dichloro(N-(1,1-dimethylethyl)-1-((1,2,3, 3a,7a-η)-1H-inden-1-yl)-1,1-dimethylsilanaminato (2-)-N)(2,2'-(1,5-pentanediyl)bis-

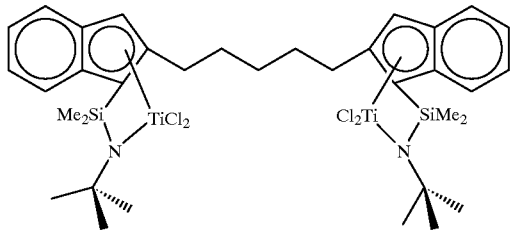

Preparation of pentamethylenebis(indene-2-yl).

2-Bromoindene (22.26 g, 114.1 mmol) and [1,3-bis (diphenylphosphino)propane]dichloronickel (II) (0.523 g, 0.965 mmol) were stirred in diethylether (150 mL) at −78° C. as pentamethylenebis(magnesium bromide) (57.1 mmol, 114.1 mL of 0.5M solution in tetrahydrofuran (THF)) was added slowly. The dry ice bath was then removed and the mixture allowed to warm slowly to about 20° C. and then for two additional hours at room temperature. After the reaction period the mixture was then poured onto ice and washed with 1 M HCl (1×100 mL), 1 M NaHCO$_3$ (1×100 mL), and then H$_2$O (1×100 mL). The organic fraction was then dried over MgSO$_4$, filtered, and the volatiles removed resulting in the isolation of a yellow oil. Recrystallization from methanol resulted in the isolation of the desired product as a white crystalline solid (7.23 g, 42.1 percent yield).

Preparation of pentamethylenebis(1-((t-butylamino) dimethylsilyl)indene-2-yl).

Pentamethylenebis(indene-2-yl) (3.001 g, 9.987 mmol) was stirred in THF (50 mL) as nBuLi (20.0 mmol, 10.00 mL of 2.0M solution in cyclohexane) was added slowly. This mixture was allowed to stir for 16 hours. This solution was then added dropwise to a solution of ClSi(CH$_3$)$_2$NH-t-Bu (3.501 g, 21.13 mmol) in THF (100 mL). This mixture was then allowed to stir for 16 hours. After the reaction period the volatiles were removed under vacuum and the residue extracted and filtered using toluene. Removal of the toluene under vacuum resulted in the isolation of the desired product as a pale yellow solid (4.827 g, 86.5 percent yield).

Preparation of tetralithio pentamethylenebis(1-((t-butylamido)dimethylsilyl)indene-2-yl)·4 THF Pentamethylenebis(1-((t-butylamino)dimethylsilyl) indene-2-yl) (3.182 g, 5.69 mmol) was stirred in THF (100 mL) as nBuLi (26.0 mmol, 13.00 mL of 2.0M solution in cyclohexane) was added slowly. This mixture was then allowed to stir overnight. After the reaction period the volatiles were removed and the residue washed well with hexane and dried under vacuum. The desired product was then isolated as a tan solid and used without further purification or analysis (4.749 g, 97.1 percent yield).

Preparation of titanium, dichloro(N-(1,1-dimethylethyl)-1-((1,2,3,3a,7a-η)-1H-inden-1-yl)-1,1-dimethylsilanaminato (2-)-N)(2,2'-(1,5-pentanediyl)bis Tetralithio pentamethylenebis(1-((t-butylamido) dimethylsilyl)indene-2-yl)·4 THF (2.647 g, 3.081 mmol) in THF (50 mL) was added dropwise to a slurry of TiCl$_3$ (THF)$_3$ (2.809 g, 7.580 mmol) in THF (100 mL). This mixture was then allowed to stir for three hours. PbCl$_2$ (2.254 g, 8.104 mmol) was then added as a solid and the mixture allowed to stir for an additional hour. After the reaction period the volatiles were removed under vacuum and the residue extracted and filtered using toluene. The toluene was then removed under vacuum and the residue slurried in hexane/CH$_2$Cl$_2$ (100 mL/25 mL), filtered, and dried under vacuum resulting in the isolation of the desired product as a red/brown microcrystalline solid (1.186 g, 48.6 percent yield).

EXAMPLE 2

Titanium, bis(trimethylsilylmethyl)(N-(1,1-dimethylethyl)-1-((1,2,3,3a,7a-η)-1H-inden-1-yl)-1, 1-dimethylsilanaminato(2-)-N)(2,2'-(1,5-pentanediyl)bis-

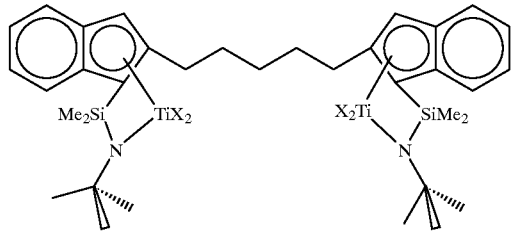

X = CH$_2$Si(CH$_3$)$_3$

Titanium, dichloro(N-(1,1-dimethylethyl)-1-((1,2,3,3a, 7a-η)-1H-inden-1-yl)-1,1-dimethylsilanaminato(2-)-N)(2, 2'-(1,5-pentanediyl)bis- (0.934 g, 1.18 mmol) was stirred in diethylether (100 mL) as MgCH$_2$Si(CH$_3$)$_3$ (4.72 mmol, 4.72 mL of 1 M solution in THF) was added dropwise. This mixture was allowed to stir overnight. After the reaction period the volatiles were removed under vacuum and the residue extracted and filtered using hexane. Removal of the hexane under vacuum resulted in the isolation of a gold solid (0.911 g, 77.3 percent yield).

Polymerization 1

A two liter reactor is charged with 750 g of Isopar E and 120 g of octene-1 comonomer. Hydrogen is added as a molecular weight control agent by differential pressure expansion from a 75 ml additional tank from 300 psig (2070 Kpa) to 275 psig (1890 Kpa). The reactor is heated to the polymerization temperature of 140° C. and saturated with ethylene at 500 psig (3450 Kpa). The appropriate amount of catalyst and cocatalyst as solutions in toluene were premixed in a glovebox and transferred to a catalyst addition tank and injected into the reactor. The polymerization conditions were maintained for 10 minutes with ethylene on demand. The resulting solution was removed from the reactor into a nitrogen purged collection vessel containing about 100 ml of isopropyl alcohol and 20 ml of about a 10 weight percent toluene solution of hindered phenol antioxidant (Irganox™ 1010 from Ciba Geigy Corporation) and phosphorus stabilizer (Irgafos 168). Polymers formed are dried in a programmed vacuum oven with a maximum temperature of 120° C. and about a 20 hours heating cycle. Results are shown in Table 1.

TABLE 1

| Run | Complex (umole) | cocat. (umole) | Yield (g) | Eff.[1] | MI[2] | density[3] | Mw/Mn |
|---|---|---|---|---|---|---|---|
| 1 | Ex. 1 (2) | MAO[4] (2000) | 18.4 | 47 | 2.42 | — | — |
| 2 | Ex. 1 (2) | MAO[5] (2000) | 13.0 | 68 | 2.73 | — | — |
| 3 | Ex. 2 (2) | FAB[6] (4) | 10.6 | 28 | .70 | 0.881 | 2.3 |
| 4 | Ex. 2 (4)[7] | ATPFB[8] (8) | 9.0 | 23 | .45 | 0.879 | 2.1 |

[1]efficiency Kg polymer/g Ti
[2]melt index, dg/min, measured by micromelt indexer technique
[3](g/cm$^3$)
[4]methylalumoxane
[5]methylalumoxane premixed with metalcomplex 15 minutes before addition to reactor
[6]tris(pentafluorophenyl)borane premixed with metalcomplex 20 minutes before addition to reactor
[7]catalyst/cocatalyst mixture added twice in equal volume injections at initiation and approximately 5 minutes after initiation of the polymerization.
[8]dimethylanilinium tetrakis(pentafluorophenyl)borate premixed with metalcomplex 20 minutes before addition to reactor

EXAMPLE 3

($\mu$-((1,1'-(1,6-hexanediyl)bis(N-(1,1-dimethylethyl)-1-methyl-1-((1,2,3,3a,7a-$\eta$)-3-(1-pyrrolidinyl)-1H-inden-1-yl)silanaminato-$\kappa$N)(4-)))) tetrachlorodititanium

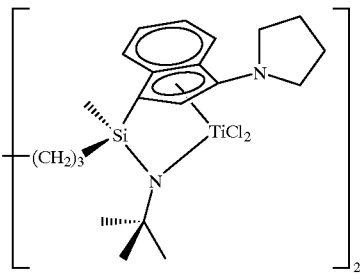

A) 1,1'-(1,6-hexanediyl)bis(1-chloro-N-(1,1-dimethylethyl)-1-methyl)-silanamine.

To a −10° C. solution of 1,6-bis(chloromethylsilyl)hexane (25.00 g, 80.1 mmol) and triethylamine (24.6 mL, 0.176 mole) in 250 mL of dichloromethane was added dropwise over 1 hour a solution of tert-butylamine (16.8 mL, 0.160 mole) in 100 mL of dichloromethane. The suspension was allowed to warm to room temperature. After stirring overnight, most to the volatiles were removed in vacuo. The product was extracted into 175 mL of hexanes, filtered and the hexanes removed in vacuo to leave 29.5 g (96 percent yield) of 1,1'-(1,6-hexanediyl)bis(1-chloro-N-(1,1-dimethylethyl)-1-methyl)silanamine as a pale-pink viscous liquid.

$^1$H NMR (C$_6$D$_6$): 1.35 (m, 4H), 1.24 (m, 4H), 1.13 (s, 18H), 1.03 (br s, 2H), 0.75 (m, 4H), 0.33 (s, 6H). $^{13}$C{$^1$H} (C$_6$D$_6$): 50.35, 33.42, 32.95, 23.74, 20.34, 3.12.

B) 1,1'-(1,6-hexanediyl)bis(N-(1,1-dimethylethyl)-1-methyl-1-(3-(1-pyrrolidinyl)-1H-inden-1-yl)-silanamine To a −30° C. solution of 1,6-bis(N-(tert-butyl)-1-chloro-1-methylsilanamine)hexane (1.50 g, 3.89 mmol) in 20 mL of THF was added a precooled (−30° C.) solution of (1-(1-pyrrolidinyl)-1H-indenyl)lithium (1.49 g, 7.78 mmol) in 10 mL of THF. The reaction was allowed to warm to room temperature as it gradually darkened and changed to a deep-red/purple solution with slight green fluorescence. After 16 hours, the volatiles were removed in vacuo and 50 mL of hexanes added. The suspension was filtered and hexanes removed from the filtrate in vacuo to leave 2.5 g (92 percent yield) of 1,1'-(1,6-hexanediyl)bis(N-(1,1-dimethylethyl)-1-methyl-1-(3-(1-pyrrolidinyl)-1H-inden-1-yl)-silanamine as a red/purple oil.

$^1$H NMR (C$_6$D$_6$): 7.71 (m, 4 H), 7.27 (m, 4 H), 5.47/5.43 (2 s, 2H, isomers), 3.51 (s, 2 H), 3.29 (br s, 8 H), 1.64 (sh m, 8 H), 1.30 (m, 8 H), 1.11 (set of several sharp peaks, 18 H), 0.616 (br s, 2H), 0.50 (s, 4H), 0.20/0.04 (2 singlets, 6H, isomers). $^{13}$C{$^1$H} (C$_6$D$_6$): 149.21, 146.99, 141.66, 124.85, 124.63, 123.95, 123.82, 120.95, 105.11, 50.86, 49.54, 43.20 (m), 34.05, 25.42, 24.51, 17.25/16.19 (isomers), −0.71/−1.88 (isomers).

C) 1,1'-(1,6-hexanediyl)bis(N-(1,1-dimethylethyl)-1-methyl-1-(3-(1-pyrrolidinyl)-1H-inden-1-yl)$^{-2}$, (deloc-1,2,3,3a,7a:1',2',3',3'a,7'a)-silanamine, dilithium, dilithium salt To a solution of 1,6-bis((N-(tert-butyl)-1-methyl-1-(3-(1-pyrrolidinyl)-1H-inden-1-yl)silanamine))hexane (2.45 g, 3.6 mmole) in 50 mL of toluene was added over 15 minutes a solution of n-butyl lithium in hexanes (1.60 M, 9.42 mL, 15.0 mmol). Over the period of addition, the original red solution turns orange followed by formation of a yellow precipitate. After stirring for 14 hours, the yellow precipitate was collected by filtration and washed twice with 10 mL of toluene and then twice with 10 mL of hexanes. The dark yellow solid was dried in vacuo for 8 hours to leave 2.6 g (quantitative yield) of the desired product.

D) ($\mu$-((1,1'-(1,6-hexanediyl)bis(N-(1,1-dimethylethyl)-1-methyl-1-((1,2,3,3a,7a-$\eta$)-3-(1-pyrrolidinyl)-1H-inden-1-yl)silanaminato-$\kappa$N)(4-))))tetrachlorodititanium To a precooled (−30° C.) suspension of TiCl$_3$(THF)$_3$ (1.42 g, 3.82 mmol) in 30 mL of THF was added a precooled (−30° C.) 30 mL THF solution of 1,6-bis((N-(tert-butyl)-1-methyl-1-(3-(1-pyrrolidinyl)-1H-inden-1-yl)silanamine)) hexane, tetralithium salt (1.35 g, 1.91 mmol). Immediately the color changed to very dark blue/green. After stirring at room temperature for 45 minutes, PbCl$_2$ (0.8 g, 2.879 mmol) was added. The color gradually changed to dark blue/purple as lead balls formed. After 1 hour, the volatiles were removed in vacuo and the product extracted into 25 mL of toluene, filtered and the volatiles removed in vacuo. The dark blue/purple residue was dried in vacuo for 4 hours and then triturated in hexanes (30 mL). The hexanes were removed in vacuo and 30 mL of hexanes was added followed by trituration again. The resulting purple/black suspension was filtered, the solid washed with hexanes and dried in vacuo overnight to leave 1.42 g (83 percent yield) of the desired product as a purple/black solid.

$^1$H NMR (C$_6$D$_6$): 7.62 (br s, 4H), 7.08 (br s, 4H), 5.67 (m, 2H), 3.58 (br s, 4H), 3.22 (br s, 4H), 1.49 (br s, 36 H), 1.8–0.50 (m, 23 H). $^{13}$C{$^1$H} (C$_6$D$_6$): 149.7 (m), 136.5, 135.5, 129.04, 128.9, 127.2, 126.4, 125.3, 106.77/106.29 (isomers), 92.3, 60.9, 50.6, 25.7, 24.3/24.0 (isomers), 19.7, 18.19, 14.34, 1.87/−0.54 (isomers).

EXAMPLE 4

(μ-((1,1'-(1,6-hexanediyl)bis(N-(1,1-dimethylethyl)-1-methyl-1-((1,2,3,3a,7a-η)-3-(1-pyrrolidinyl)-1H-inden-1-yl)silanaminato-κN)(4-))))tetramethyldititanium

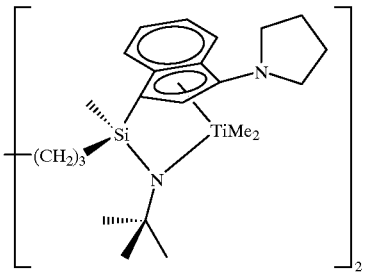

To a suspension of (μ((1,1'-(1,6-hexanediyl)bis(N-(1,1-dimethylethyl)-1-methyl-1-((1,2,3,3a,7a-η)-3-(1-pyrrolidinyl)-1H-inden-1-yl)silaninato-κN) (4-)))) tetrachlorodititanium (0.189 g, 0.21 mmol) in 10 mL os diethyl ether was added a solution of MeLi (1.4 M/Et$_2$O, 0.59 mL, 0.82 mmol). Instantly the solution turned dark red. After stirring at room temperature for 1 hour, the volatiles were removed in vacuo and the product extracted into 20 mL of hexanes. The suspension was filtered and the brown filter cake washed until no appreciable red color appeared in the washing. The volatiles were removed from the red filtrate and the residue dried in vacuo for 1 hour. The residue was extracted into hexanes (15 mL) and filtered to remove trace amounts of fine particulates. The hexanes were removed from the filtrate in vacuo and the resulting red 'flaky' solid dried in vacuo overnight to leave 0.130 g (75 percent yield) of red solid.

$^1$H NMR (C$_6$D$_6$): 7.73 (m, 2H), 7.50 (m, 2H), 7.04 (m, 2H), 6.89 (m, 2H), 5.42 (m, 2H), 3.43 (m, 4H), 3.25 (m, 4H), 1.53 (sh m, 36 H), 1.8–0.50 (m, 20 H), 0.09 (br s, 6H). $^{13}$C{$^1$H} (C$_6$D$_6$): 144.16 (m), 133.99, 133.31, 125.60, 125.13, 124.73, 123.90, 104.642, 104.02, 83.90, 57.78, 54.34, 54.13, 50.63, 48.86, 34.91, 33.99, 33.86, 26.05, 24.73, 24.38, 20.84, 19.20, 2.86, 0.39.

EXAMPLE 5

(μ-((1,1'-(1,2-ethanediyl)bis(N-(1,1-dimethylethyl)-1-methyl-1-((1,2,3,3a,7a-η)-3-(1-pyrrolidinyl)-1H-inden-1-ylsilanaminato-κN)(4-))))tetrachlorodititanium

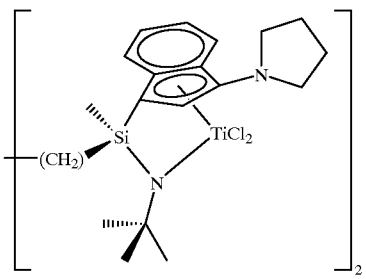

A) 1,1'-(1,2-ethanediyl)bis(1-chloro-N-(1,1-dimethylethyl)-1-methyl)silanamine

To a –10° C. solution of and 1,6-bis(dichloromethylsilyl)ethane (5.00 g, 19.5 mmol) and triethylamine (6.0 mL, 43 mmol) in 50 mL of CH$_2$Cl$_2$ was added dropwise over 1 hour a solution of tert-butylamine (4.1 mL, 39.0 mmol) in 20 mL of CH$_2$Cl$_2$. The obtained white suspension was allowed to warm to room temperature. After stirring for 16 hours, most of the solvent was removed in vacuo and 75 mL of hexanes added. The resulting suspension was filtered and the volatiles removed from the filtrate in vacuo to leave 1,6-bis(N-(tert-butyl)-1-chloro-1-methylsilanamine)ethane (5.7 g, 97 percent yield) as a pale pink oily solid.

$^1$H NMR (C$_6$D$_6$): 1.12 (s, 18H), 1.03 (br s, 2H), 0.91 (m, 4H), 0.33/0.32. (two s, 6H, isomers). $^{13}$C{$^1$H} (C$_6$D$_6$): 50.36, 33.32, 32.95,12.65/12. (two peaks/isomers), 2.39/2.13 (two peaks/isomers).

B) 1.1'-(1,2-ethanediyl)bis(N-(1,1-dimethylethyl)-1-methyl-1-(3-(1-pyrrolidinyl)-1H-inden-1-yl)-silanamine To a –30° C. solution of (1-(1-pyrrolidinyl)-1H-indenyl)lithium (1.705 g, 8.92 mmol) in 10 mL of THF was added a –30° C. solution of 1,6-bis(N-(tert-butyl)-1-chloro-1-methylsilanamine)ethane (1.47 g, 4.46 mmol) in 5 mL of THF. The reaction was allowed to warm to room temperature as it gradually darkened and changed to a deep-red/purple solution with slight green fluorescence. After 16 hrs at room temperature, the volatiles were removed in vacuo and then 50 mL of hexanes was added. The suspension was filtered and the hexanes removed from the filtrate in vacuo to leave 1,6-bis((N-(tert-butyl)-1-methyl-1-(3-(1-pyrrolidinyl)-1H-inden-1-yl)silanamine)ethane (2.7 g, 97% yield) as a red/purple oil.

$^1$H NMR (C$_6$D$_6$): 7.75–7.55 (m, 4H), 7.40–7.15 (m, 4H), 5.42 (m, 2H), 3.505 (m, 2 H), 3.29 (br s, 8 H), 1.65 (br s, 8 H), 1.09 (set of several sharp peaks, 18 H), 0.88 (m, 2H), 0.54 (m, 4H), 0.45–0.00 (m, 6H). $^{13}$C{$^1$H} (C$_6$D$_6$): 149.07, 147.03, 141.59, 124.58, 124.39, 123.98, 123.78, 120.92, 105.22, 50.86, 49.49, 42.80 (m), 34.13, 25.43, 11.0–8.0 (m), 0.0-(–3.0) (m).

C) 1,1'-(1,2-ethanediyl)bis(N-(1,1-dimethylethyl)-1-methyl-1-(3-(1-pyrrolidinyl)-1H-inden-1-yl)$^{-2}$, (deloc-1,2,3,3a,7a:1',2',3',3'a,7'a)-silanamine, dilithium, dilithium salt To a stirred solution of 1,6-bis((N-(tert-butyl)-1-methyl-1-(3-(1-pyrrolidinyl)-1H-inden-1-yl)silanamine))ethane (2.7 g, 4.31 mmol) in 50 mL of toluene was added n-BuLi (11.3 ml, 1.6 M, 18.1 mmol) over fifteen minutes. The original red solution slowly turned to a orange-yellow suspension over one hour. After 16 hours, the yellow/orange suspension was filtered and washed with toluene until the washings became colorless (4×5 mL washes). The sample was then washed 3 times with 20 mL of hexanes and dried in vacuo for 5 hours to leave 2.60 g (93 percent yield) of 1,6-bis((N-(tert-butyl)-1-methyl-1-(3-(1-pyrrolidinyl)-1H-inden-1-yl)silanamine))ethane, tetralithium salt as a fine yellow powder.

D) (μ-((1,1'-(1,2-ethanediyl)bis(N-(1,1-dimethylethyl)-1-methyl-1-((1,2,3,3a,7a-η)-3-(1-pyrrolidinyl)-1H-inden-1-yl)silanaminato-κN)(4-))))tetrachlorodititanium To a precooled (–30° C.) suspension of TiCl$_3$(THF)$_3$ (1.27 g, 3.44 mmol) in 20 mL of THF was added a precooled (–30° C.) 20 mL THF solution of 1,6-bis((N-(tert-butyl)-1-methyl-1-(3-(1-pyrrolidinyl)-1H-inden-1-yl)silanamine)) ethane, tetralithium salt (1.12 g, 1.72 mmol). Immediately the color changed to very dark blue/green. After stirring at room temperature for 1 hour, PbCl$_2$ (0.67 g, 2.4 mmol)was added. The color gradually changed to dark blue/purple as lead particles formed. After 1 hour, the volatiles were removed in vacuo and the residue dried in vacuo for 1 hour. The product was extracted into 60 mL of toluene, filtered and the volatiles removed in vacuo. After drying the dark residue in vacuo for an hour, hexanes (20 mL) was added and the dark solid triturated. The volatiles were removed in vacuo, 20 mL of hexanes were added and the solid triturated again. The resulting purple/black suspension was filtered and the solid washed twice with 3 mL of hexanes and dried in vacuo overnight to leave 1.35 g (91 percent yield) of the desired product as a dark purple solid.

$^1$H NMR (C$_6$D$_6$): 7.80–7.55 (m, 4H), 7.30–6.70 (m, 4H), 5.75 (m, 2H), 3.75–3.00 (m, 4H), 1.45 (br s, 36 H), 1.90–0.50 (m, 15 H). $^{13}C\{^1H\}$ ($C_6D_6$): 149.9 (m), 136.4, 135.5, 129.5, 129.3, 129.1, 127.4, 126.6, 126.4, 126.1, 106.1 (m), 92.4, 61.1, 50.7, 33.3, 25.9, 15–9 (m), 0.92/0.81/–1.19 (isomers).

EXAMPLE 6

($\mu$((1,1'-(1,2-ethanediyl)bis(N-(1,1-dimethylethyl)-1-methyl-1-((1,2,3,3a,7a-$\eta$)-3-(1-pyrrolidinyl)-1H-inden-1-yl)silanaminato-$\kappa$N)(4-))))tetramethyldititanium

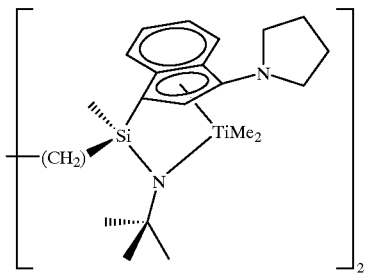

To a suspension of (R-((1,1'-(1,2-ethanediyl)bis(N-(1,1-dimethylethyl)-1-methyl-1-((1,2,3,3a,7a-$\eta$)-3-(1-pyrrolidinyl)-1H-inden-1-yl)silanaminato-$\kappa$N)(4-)))) tetrachlorodititanium (0.430 g, 0.50 mmol) in 25 mL of diethyl ether was added a solution of MeLi (1.4 M/Et$_2$O, 1.43 mL, 2.00 mmol). Instantly the solution turned dark red. After stirring at room temperature for 1 hour, the volatiles were removed in vacuo and the sample dried in vacuo for 1 hour. The product was extracted into 50 mL of hexanes, the suspension filtered and the brown filter cake washed until no appreciable red color appeared in the washing. The volatiles were removed from the red filtrate and the residue dried in vacuo for 2 hours. The residue was extracted again into hexanes (15 mL) and filtered to remove trace amounts of an insoluble brown residue. The hexanes were removed from the filtrate in vacuo and the resulting red solid dried in vacuo overnight to leave 0.280 g (67 percent yield) of red solid.

$^1$H NMR ($C_6D_6$): 7.85–7.45 (m, 4H), 7.10–6.65 (m, 4H), 5.56 (m, 2H), 3.46 (s, 4H), 3.28 (br m, 4H), 1.55 (sh m, 36 H), 1.8–0.50 (m, 12 H), 0.09 (m, 6H). $^{13}C\{^1H\}$ ($C_6D_6$): 144.2 (m), 134.1, 133.8, 126.0–124.0 (m), 104.6 (m), 83.85 (m), 57.89 (m), 54.5 (m), 50.52 (m), 51.0–49.0 (m), 34.99, 26.09, 15.0–10.0 (m), 2.0 (m), –0.40 (m).

EXAMPLE 7

($\mu$-((1,1'-(1,6-hexanediyl)bis(N-(1,1-dimethylethyl)-1-methyl-1-((1,2,3,4,5-$\eta$)-2,3,4,5-tetramethyl-2,4-cyclopentadien-1-yl)silanaminato-$\kappa$N)(4-))))tetrakis(phenylmethyl)dititanium

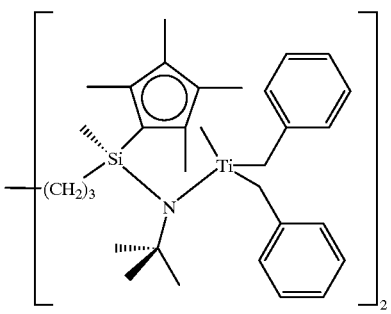

A) 1,6-hexanediylbis(chloromethyl(2,3,4,5-tetramethyl-2,4-cyclopentadien-1-yl)silane To a –10° C. solution of 1,6-bis(dichloromethylsilyl)hexane in 50 mL of THF was added dropwise over 1 hour a 30 mL THF solution of (2,3,4,5-tetramethycyclopentadienyl) magnesium-bromide·(THF)$_x$ (1.75 g, 5.49 mmol, 319 g/mol effective MW). The nearly colorless reaction was allowed to slowly warm to room temperature. After stirring overnight, the volatiles were removed in vacuo. The product was extracted into 75 mL of hexanes, filtered and the filter cake washed several times with hexanes. The volatiles were removed from the filtrate in vacuo to leave 1.25 g (94 percent yield) of 1,6-bis(1-(1,2,3,4-tetramethylcyclopentadienyl)-1-chloro-1-methylsilyl) hexane as a off-white waxy solid.

$^1$H NMR ($C_6D_6$): 2.99 (br s, 2H), 1.98 (overlapping s, 12H), 1.754 (s, 12H), 1.50–1.10 (m, 8 H), 0.80–0.50 (m, 4 H), 0.19 (s, 6 H). $^{13}C\{^1H\}$ ($C_6D_6$): 137.87, 131.65, 55.98, 33.12, 23.64, 16.74, 14.67, 11.51, –0.64.

B) 1,1'-(1,6-hexanediyl)bis(N-(1,1-dimethylethyl)-1-methyl-1-(2,3,4,5-tetramethyl-2,4-cyclopentadien-1-yl) silanamine To a solution of triethylamine (0.9 mL, 6.46 mmol) and 1,6-bis(1-(1,2,3,4-tetramethylcyclopentadienyl)-1-chloro-1-methylsilyl)hexane (1.25 g, 2.58 mmol) in 30 mL of CH$_2$Cl$_2$ was added tert-butylamine (0.6 mL, 5.69 mmol) all at once. The solution became cloudy as white precipitate formed. After stirring at room temperature for 2 hours, the volatiles were removed in vacuo and hexanes were added (30 mL). The hexanes extract was filtered and the filter cake washed twice with hexanes. The volatiles were removed from the filtrate in vacuo to leave 1.4 g (97 percent yield) of 1,6-bis(N-(tert-butyl)-1-(1,2,3,4-tetramethyl-cyclopentadienyl)-1-methylsilanamine)hexane as a pale-yellow, viscous oil.

$^1$H NMR ($C_6D_6$): 2.89 (brs, 2H), 2.15–1.70 (m, 265H), 1.41 (brs, 8H), 1.12 (s, 18H), 0.58/0.40 (m, 4H), 0.24 (s, 6 H). $^{13}C\{^1H\}$ ($C_6D_6$): 135.50, 133.47, 133.13, 56.37, 49.49, 34.03, 33.88, 24.61, 23.93, 17.12, 15.28/15.18, 11.61, 0.50.

C) ($\mu$-((1,1'-(1,6-hexanediyl)bis(N-(1,1-dimethylethyl)-1-methyl-1-((1,2,3,4,5-$\eta$)-2,3,4,5-tetramethyl-2,4-cyclopentadien-1-yl)silanaminato-$\kappa$N)(4-))))tetrakis(phenylmethyl)di-titanium A Schlenk flask was charged with a hexanes solution (80 mL) of tetra(benzyl) titanium (1.433 g, 3.47 mmol) and 1,6-bis(N-(tert-butyl)-1-(tetramethylcyclopentadienyl)-1-methylsilanamine)hexane (0.88 mg, 1.58 mmol). The reaction was heated to 60° C. for 22 hours. The reaction was taken into the glovebox and heated to reflux for 4 hours. The volatiles were removed in vacuo, the residue extracted with hexanes (75 mL), filtered and the volatiles removed in vacuo. The residue was again extracted into hexanes (50 mL), filtered, and the filtrate concentrated to about 10 mL. After cooling the solution at –30° C. overnight, the mother liquor was filtered and the oily dark solid washed twice with 5 mL of hexanes. The volatiles were removed from the filtrate in vacuo to leave 1.2 g (75 percent yield) of the desired product as an oily gold-brown solid.

$^1$H NMR ($C_6D_6$): 7.13 (m, 8H), 6.85 (m, 12 H), 3.0–0.0 (several overlapping multiplets with distinct peaks at around 1.75, 1.45 and 0.5 ppm). $^{13}C\{^1H\}$ ($C_6D_6$): 150.35, 134.92, 134.32, 131.85 (m), 128.35, 127.15 (brs), 122.92, 122.34, 83.10, 82.06, 84–80 (underlying mult.), 60.18, 38.5, 36.75, 34.49, 33.92, 16.0–11.0 (m), 3.45.

EXAMPLE 8

(μ-((1,1'-(1,2-ethanediyl)bis(N-(1,1-dimethylethyl)-
1-methyl-1-((1,2,3,4,5-η)-2,3,4,5-tetramethyl-2,4-
cyclopentadien-1-yl)silanaminato-κN)(4-))))tetrakis
(phenylmethyl)dititanium

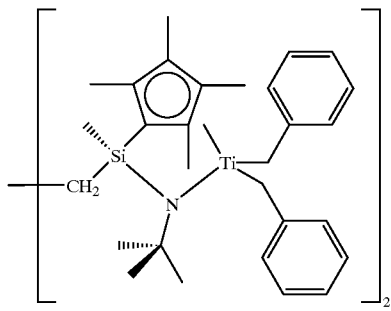

A) 1,2-ethanediylbis(chloromethyl(2,3,4,5-tetramethyl-2,4-cyclopentadien-1-yl)silane To a 0° C. solution of 1,6-bis(dichloromethylsilyl)ethane (5.73 g, 22.4 mmol) in 100 mL of THF was added dropwise over 1.5 hour a 300 mL THF solution of (2,3,4,5-tetramethylcyclopentadienyl)magnesiumchloride·(THF)$_x$ (11.06 g, 44.8 mmol, 247 g/mol effective MW). The reaction was allowed to slowly warm to room temperature overnight. After 17 hours, the volatiles were removed in vacuo and the resulting off white solid dried in vacuo for an additional hour. To the solid was added 150 mL of hexanes and the suspension vigorously stirred for 10 minutes. The suspension was filtered and the volatiles removed in vacuo from the pale yellow filtrate. After thorough drying, 9.41 g (98 percent yield) of the desired product was obtained as an off-white solid.

$^1$H NMR (C$_6$D$_6$): 2.97 (brs, 2H), 1.99 (s, 6H), 1.92 (s, 6H), 1.74 (s, 12H), 0.9–0.5 (m, 4H), 0.15 (s, 6H). $^{13}$C{$^1$H} (C$_6$D$_6$): 138.02, 131.58 (br), 55.67, 14.67, 11.52, 9.13, –1.18.

B) 1,1'-(1,6-ethanediyl)bis(N-(1,1-dimethylethyl)-1-methyl-1-(2,3,4,5-tetramethyl-2,4-cyclopentadien-1-yl)silanamine To a solution of triethylamine (7.7 mL, 55 mmol) and 1,2-ethanediylbis(chloromethyl-(2,3,4,5-tetramethyl-2,4-cyclopentadien-1-yl)-silane (9.4 g, 21.98 mmol) in 80 mL of CH$_2$Cl$_2$ was added tert-butylamine (5.1 mL, 48 mmol) all at once. A white suspension quickly formed. After stirring for three hours, the volatiles were removed in vacuo and the product into hexanes (120 mL). The suspension was filtered and washed twice with 10 mL of hexanes. The hexanes were remove in vacuo to leave 10.33 g (100 percent yield) of 1,6-bis(N-(tert-butyl)-1-(1,2,3,4-tetramethyl-cyclopentadienyl)-1-methylsilanamine)ethane as a pale-yellow, viscous oil.

$^1$H NMR (C$_6$D$_6$): 2.90/2.82 (two s, 2H, isomers), 2.10–1.70 (m, 26H), 1.13/1.10 (two s, 18H, isomers), 0.46 (m, 4H), 0.30–0.15 (m, 6H). $^{13}$C{$^1$H} (C$_6$D$_6$): 135.4 (m), 133.67, 133.22, 56.14 (m), 49.37, 33.95, 15.05 (m), 11.46, 9.01 (m), –0.20 (m).

C) (μ-((1,1'-(1,2-ethanediyl)bis(N-(1,1-dimethylethyl)-1-methyl-1-((1,2,3,4,5-1)-2,3,4,5-tetramethyl-2,4-cyclopentadien-1-yl)silanaminato-κN)(4-))))tetrakis(phenylmethyl)dititanium A Schienk flask was charged with a hexanes solution (90 mL) of tetra(benzyl) titanium (1.97 g, 4.78 mmol) and 1,6-bis(N-(tert-butyl)-1-(Me$_4$Cp)-1-methylsilanamine) ethane (1.022 g, 2.17 mmol). The reaction was heated to 60° C. for 19 hours and the resulting dark yellow/brown solution was then heated to reflux for an additional four hours. The volatiles were removed in vacuo and the product extracted into hexanes (100 mL). The suspension was filtered to remove some black solid and the volatiles were removed from the filtrate. The residue was dried in vacuo for one hour and then extracted with hexanes again (70 mL). The suspension was filtered and the volatiles removed from the filtrate. The residue was again extracted with hexanes (50 mL), filtered and the filtrate concentrated to about 20 mL. The dark solution was cooled at –30° C. overnight. The solution was decanted away from the black oily residue and the residue washed twice with 5 mL of hexanes. The hexanes filtrate was concentrated to 5 mL and cooled at –30° C. overnight. The solution was filtered and the small amount of black insoluble residue was washed with hexanes. The volatiles were removed from the hexanes filtrate in vacuo and the solid dried in vacuo for 5 hours to leave 1.25 g (62 percent yield) of desired complex as a dark gold-brown solid.

$^1$H NMR (C$_6$D$_6$): 7.13 (m, 8H), 6.85 (m, 12 H), 3.0–0.0 (several overlapping multiplets with distinct peaks at around 1.75, 1.45 and 0.5 ppm). $^{13}$C{$^1$H} (C$_6$D$_6$): 150.35, 134.92, 134.32, 131.85 (m), 128.35, 127.15 (brs), 122.92, 122.34, 83.10, 82.06, 84–80 (underlying multiplets), 60.18, 38.5, 36.75, 34.49, 33.92, 16.0–11.0 (m), 3.45.

EXAMPLE 9 bis(1,1'-(η$^4$-1,3-butadiene-1,4-diyl)bis(benzene))(μ-
(1,6-hexanediylbis((methylsilylidyne)bis((1,2,3,3a,
7a-η)-2-methyl-4-phenyl-1H-inden-1-ylidene))))
dizirconium

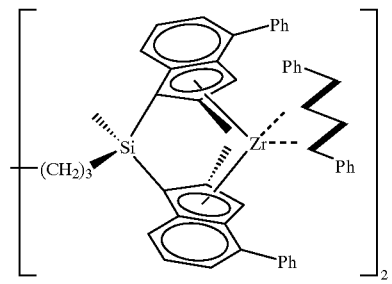

A) Lithium 2-methyl-4-phenylindenide.

To a solution of 2-methyl-4-phenylindene (10.03 g, 49.3 mmol) in 200 mL of hexanes was added dropwise over 10 minutes 32 mL of 1.6M n-BuLi. The resulting yellow suspension was stirred for 17 hours. The suspension was filtered and the solid washed twice with 5 mL of hexane. The light yellow solid was dried in vacuo for 2 hours to leave 9.21 g (89 percent yield) of lithium 2-methyl-4-phenylindenide. A second crop (0.61 g) was obtained by concentrating the filtrate to about 80 mL and filtering after 4 hours at room temperature. Overall yield was 9.82 g, 95 percent.

B) 1,6-hexanediylbis(methylbis(2-methyl-4-phenyl-1H-inden-1-yl)-silane

A solution of 1,6-bis(dichloromethylsilyl)hexane (1.78 g, 5.69 mmol) in 20 mL of toluene was added dropwise over 30 minutes to a solution of lithium 2-methyl-4-phenylindenide (5.00 g, 23.9 mmol) in 60 mL of THF. The cloudy orange solution was left to stir at room temperature for 20 hours and then quenched by slow addition of water (80 mL). Most of the THF was removed by rotary evaporation and the product extracted into diethyl ether (120 mL). The organic/aqueous layers were separated and the aqueous layer washed twice with 50 mL of diethyl ether. The organic extracts were combined, dried over MgSO$_4$, filtered and most of the volatiles removed in vacuo. The reaction residue was dissolved in enough toluene to make about 25 mL of a viscous solution. The reaction mixture was subsequently chromatographed on silica (35 cm×5 cm column) initially eluting with hexanes followed by 4:1 hexanes:CH$_2$Cl$_2$ to remove excess 2-methyl-4-phenylindene (Rf=0.62 (silica, 2:1 hexanes:dichloromethane). Further elution with 4:1 hexanes:CH$_2$Cl$_2$ gave one fraction of the desired product 1,6-bis[methylsilyl-bis(2-methyl-4-phenylindenyl)hexane (Rf≅0.38 silica, 2:1 hexanes:dichloromethane) which was isolated by removal of volatiles in vacuo to leave 1.53 g (27%) of pale yellow solid. Further elution with 3:1 hexanes:CH$_2$Cl$_2$ led to isolation of a second fraction which has a much broader elution bandwidth (Rf≅0.35–0.10). Removal of volatiles in vacuo from the sample gave 1.89 g (34 percent) of pale yellow solid. Overall yield was 3.42 g (61 percent).

$^1$H NMR (CDCl$_3$): 7.70–6.9 (m, 32H), 6.74 (m, 4H), 4.0–3.5 (m, 4H), 2.4–1.9 (m, 12H), 1.6–0.4 (m, 12H), 0.45-(−0.2) (m, 6H). $^{13}$C{$^1$H} (CDCl$_3$): 158.2, 150.9, 148.2, (m), 145.9, 143.1 (m), 141.6 (m), 140.55, 137.6, 134.31, 130–120 (several multiplets.), 77.1 (m), 48.9, 47.3 (m), 33.5, 24.1, 18.1 (m), 15.1 (m), 13.2 (m), 12.4 (m), −5.4 (m).

B) 1,6-hexanediylbis(methylbis(2-methyl-4-phenyl-1H-inden-1-yl)-silane, ion(4-), tetralithium To a 20 mL toluene solution of 1,6-bis[methylsilyl-bis(2-methyl-4-phenyl-indenyl)hexane (1.01 g, 1.04 mmol) was added n-butyl lithium over 10 minutes (2.7 mL, 1.6 M in hexanes, 4.29 mmol). After 20–30 minutes, a yellow precipitate began to form. After stirring for 18 hours at room temperature, the yellow-orange suspension was filtered and washed twice with 6 mL of toluene then twice with 5 mL of hexane. The sample was dried in vacuo for 5 hours until the weight of sample stabilized to leave 0.91 g (89 percent yield) of tetralithium 1,6-bis[methylsilyl-bis(2-methyl-4-phenyl-indenylide)hexane as a yellow powder.

C) bis(1,1'-(η$^4$-1,3-butadiene-1,4-diyl)bis(benzene))(4-(1,6-hexanediylbis((methylsilylidyne)bis((1,2,3,3a,7a-η)-2-methyl-4-phenyl-1H-inden-1-ylidene))))dizirconium To a −30° C. suspension of tetralithium 1,6-bis [methylsilyl-bis(2-methyl-4-phenyl-indenylide)hexane (0.300 mg, 0.30 mmol) in 5 mL of toluene was added a −30° C. solution of bis(triethylphosphine)(1,4-diphenylbutadiene) zirconium dichloride (0.432 g, 0.60 mmol) in 10 mL of toluene. The reaction was allowed to slowly warm to room temperature as the dark purple/black solution turned red. After stirring overnight, the solution was filtered and the volatiles removed in vacuo. The reaction residue was dissolved in 40 mL of toluene and added dropwise to 60 mL of hexanes. An additional 50 mL of 3:2 hexanes:toluene solvent mixture was added and the resulting orange/brown precipitate filtered and washed extensively with hexanes (3×30 mL). The volatiles were removed from the dark red filtrate and the oily red solid triturated with 10 mL of hexanes and the volatiles removed in vacuo. The trituration was repeated once more with 10 mL of hexanes and the obtained solid was filtered and washed with 5 mL of hexanes. The deep red solid was dried in vacuo overnight to leave 0.306 g (65 percent) of the desired product.

$^1$H NMR (CDCl$_3$): 8.0–7.6 (m, 4 H), 7.6–6.6 (m, 52H), 5.6 (br s, 4H), 3.4 (m, 4H), 2.1–0.5 (m, 30H). $^{13}$C{$^1$H} (C$_6$D$_6$): 158.2, 150.9, 148.2 (m), 145.9, 143.1 (m), 141.6 (m), 140.55, 137.6, 134.31, 130–120 (several multiplets.), 77.1 (m), 48.9, 47.3 (m), 33.5, 24.1, 18.1 (m), 15.1 (m), 13.2 (m), 12.4 (m), −5.4 (m).

EXAMPLE 10

(μ-((1,1'-(1,6-hexanediyl)bis(N-(1,1-dimethylethyl)-1-methyl-((1,2,3,3a,7a-η)-1H-inden-1-yl) silanaminato-κN)(4-))))tetrachlorodititanium

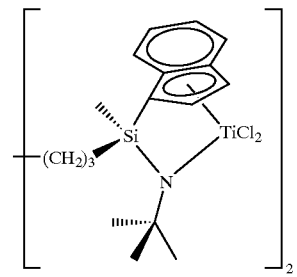

A) 1,1'-(1,6-hexanediyl)bis(1-chloro-N-(1,1-dimethylethyl)-1-methyl)-silanamine.

This intermediate was prepared as in Example 3, step A).

B) 1,1'-(1,6-hexanediyl)bis(N-(1,1-dimethylethyl)-1-methyl-1H-inden-1-yl)-silanamine The reaction conditions of Example 3B) were substantially repeated using (1H-indenyl)lithium (in 10 mL of THF).

C) 1,1'-(1,6-hexanediyl)bis(N-(1,1-dimethylethyl)-1-methyl-1H-inden-1-yl)$^2$. (deloc-1,2,3,3a,7a:1',2',3',3'a,7'a)-silanamine, dilithium, dilithium salt To a solution of 1,6-bis((N-(tert-butyl)-1-methyl-1H-inden-1-yl)silanamine))hexane in toluene was added over 15 minutes a solution of 4 equivalents of n-butyl lithium in hexanes. Over the period of addition, the original red solution turns orange followed by formation of a yellow precipitate. After stirring for 14 hours, the yellow precipitate was collected by filtration and washed twice with 10 mL of toluene and then twice with 10 mL of hexanes. The dark yellow solid was dried in vacuo for 8 hours to leave 2.6 g (quantitive yield) of the desired product.

D) (μ-((1,1'-(1,6-hexanediyl)bis(N-(1,1-dimethylethyl)-1-methyl-1-((1,2,3,3a,7a-η)-3-(1-pyrrolidinyl)-1H-inden-1-yl)silanaminato-κN)(4-))))tetrachlorodititanium To a precooled (−30° C.) suspension of TiCl$_3$(THF)$_3$ (1.42 g, 3.82 mmol) in 30 mL of THF was added a precooled (−30° C.) 30 mL THF solution of 1,6-bis((N-(tert-butyl)-1-methyl-1-(3-(1-pyrrolidinyl)-1H-inden-1-yl)silanamine)) hexane, tetralithium salt (1.35 g, 1.91 mmol). Immediately the color changed to very dark blue/green. After stirring at room temperature for 45 minutes, PbCl$_2$ (0.8 g, 2.879 mmol) was added. The color gradually changed to dark blue/purple as lead balls formed. After 1 hour, the volatiles were removed in vacuo and the product extracted into 25 mL of toluene, filtered and the volatiles removed in vacuo. The dark blue/purple residue was dried in vacuo for 4 hours and then triturated in hexanes (30 mL). The hexanes were removed in vacuo and 30 mL of hexanes was added followed by trituration again. The resulting purple/black suspension was filtered, the solid washed with hexanes and dried in vacuo overnight to leave 1.42 g (83 percent yield) of the desired product as a purple/black solid.

$^1$H NMR (C$_6$D$_6$): 7.62 (br s, 4H), 7.08 (br s, 4H), 5.67 (m, 2H), 3.58 (br s, 4H), 3.22 (br s, 4H), 1.49 (br s, 36H), 1.8–0.50 (m, 23H). $^{13}$C{$^1$H} (C$_6$D$_6$): 149.7 (m), 136.5, 135.5, 129.04, 128.9, 127.2, 126.4, 125.3, 106.77/106.29 (isomers), 92.3, 60.9, 50.6, 25.7, 24.3/24.0 (isomers), 19.7, 18.19, 14.34, 1.87/–0.54 (isomers).

Polymerization 2

A two liter reactor is charged with 750 g of Isopar E and 120 g of octene-1 comonomer. Hydrogen is added as a molecular weight control agent by differential pressure expansion from a 75 ml additional tank from 300 psig (2070 Kpa) to 275 psig (1890 Kpa). The reactor is heated to the polymerization temperature of 140° C. and saturated with ethylene at 500 psig (3450 Kpa). The appropriate amount of catalyst and cocatalyst (trispentafluorophenyl)borane as 0.005 M solutions in toluene (approximately 4 pmole complex based on metal content) were premixed in a glovebox to give a 1:2 molar ratio of catalyst and cocatalyst, and transferred to a catalyst addition tank and injected into the reactor. The polymerization conditions were maintained for 10 minutes with ethylene on demand. The resulting solution was removed from the reactor into a nitrogen purged collection vessel containing 100 ml of isopropyl alcohol and 20 ml of a 10 weight percent toluene solution of hindered phenol antioxidant (Irganox™ 1010 from Ciba Geigy Corporation) and phosphorus stabilizer (Irgafos 168). Polymers formed are dried in a programmed vacuum oven with a maximum temperature of 120° C. and a 20 hours heating cycle. Results are shown in Table 2.

TABLE 2

| Run | complex | Efficiency[1] | MI[2] | density[3] | Mw/Mn |
| --- | --- | --- | --- | --- | --- |
| 5 | Ex. 4 | 0.6 | <0.1 | 0.911 | 294,000/106/000 |
| 6 | Ex. 6 | 0.3 | 0.1 | 0.911 | 299,000/138,000 |
| 7 | Ex. 8 | 0.4 | 1.7 | 0.900 | 108,000/43,200 |
| 8 | Ex. 7 | 0.5 | 1.9 | 0.901 | 106,000/50,600 |
| 9 | Ex. 9 | 0.8 | 9.0 | 0.892 | 69,900/28,700 |
| 10* | TTiD[4] | 0.7 | 12.1 | 0.904 | 61,900/28,200 |
| 11* | BZrD[5] | 1.8 | 10.7 | 0.886 | 67,300/29,300 |

*not an example of the invention
[1]efficiency, g polymer/μg metal
[2]melt index, dg/min, measured by micromelt indexer
[3](g/cm$^3$)
[4](t-butylamido)dimethyl(tetramethylcyclopentadienyl)silanetitanium (II) 1,3-pentadiene
[5]1,2-ethanebis(2-methyl-4-phenylinden-1-yl)zirconium (II) 1,4-diphenyl-1-3-butadiene

EXAMPLE 11

Preparation of {dimethylsilyl-N-(trans-1,4-cyclohexylene)-(tetramethylcyclopentadienyl) titanium dichloride}bis-

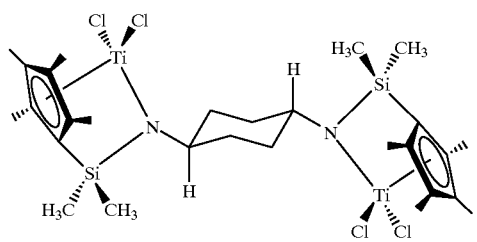

A) Dilithium trans-1,4-diamidocyclohexane

To 100 mL of (2.00 M, 200 mmol) butyl lithium in cyclohexane solution dissolved in about 300 mL of diethyl ether was added 10.5 g (92.5 mmol) of trans-1,4-diaminocyclohexane. The reaction solution gradually became thick with precipitate. The reaction mixture was heated to reflux for several hours, then allowed to cool to ambient temperature. The pale yellow slurry was then filtered, washed several times with diethyl ether, then hexane and dried under reduced pressure. The product was isolated as a white powder.

B) Trans-1,4-bis(dimethyl(2,3,4,5-tetramethylcyclopentadienyl)silylamino)cyclohexane To 3.68 g (29.2 mmol) of dilithium trans-1,4-diamidocyclohexane slurried in about 200 mL of diethyl ether was slowly added under stirring 12.5 g (58.4 mmol) of chlorodimethyl(2,3,4,5-tetramethylcyclopentadienyl)silane. The reaction mixture was allowed to stir overnight. The reaction mixture was filtered and the volatiles were removed under reduced pressure, then heated under dynamic vacuum for a few hours to remove a small amount of unreacted chlorodimethyl(2,3,4,5-tetramethylcyclopentadienyl)silane. The product was isolated as an oil. The $^1$H and $^{13}$C NMR spectra, MS analysis and C,H,N elemental analysis were all consistent with the desired product.

C) Trans-1,4-bis(dimethyl(2,3,4,5-tetramethylcyclopentadienyl)silylamino)cyclohexane To 10.0 g (79.4 mmol) of dilithium trans-1,4-diamidocyclohexane slurried in about 400 mL of THF was slowly added under stirring 34.1 g (159 mmol) of chlorodimethyl(2,3,4,5-tetramethylcyclopentadienyl)silane. The dilithium salt gradually dissolved during the course of the addition. Precipitate began to form near the end of the addition. The reaction mixture was allowed to stir overnight. The reaction mixture was filtered and the volatiles were removed under reduced pressure to give the product as a light-colored oil which was heated under dynamic vacuum for a few hours (33.1 g, 88.5%).

D) Tetralithium trans-1,4-bis(dimethyl(2,3,4,5-tetramethylcyclopentadienyl)silylamido)cyclohexane To 5.52 g (11.7 mmol) of trans-1,4-bis(dimethyl(2,3,4,5-tetramethylcyclopentadienyl)silylamino)cyclohexane in about 80 mL of diethyl ether was added 32.3 mL (1.6 M, 51.7 mmol) of butyl lithium at a rate that rapid gas evolution, but not refluxing, took place. Precipitate formed almost immediately. The reaction solution was allowed to stir overnight. The resulting slurry was filtered, the solid was washed three times with diethyl ether, then dried under reduced pressure. The product was isolated as a beige powder in essentially quantitative yield (6.86 g). NMR experiments indicated that the product contained about 1 ether molecule per product molecule.

E) Trans-1,4-bis(dimethyl(2,3,4,5-tetramethylcyclorentadienyl)silylamido)cyclohexane dititanium tetrachloride Solid tetralithium trans-1,4-bis(dimethyl(2,3,4,5-tetramethylcyclopentadienyl)silylamido)cyclohexane (2.92 g, 5.13 mmol) and solid titanium tetrachloride bis(tetrahydrofuranate) (3.43 g, 10.3 mmol) were mixed well in a flask. Upon addition of about 150 mL of toluene, an orange-red color developed which gradually became more reddish brown on stirring. The reaction mixture was allowed to stir for several days. The reddish-orange reaction solution was filtered and all volatiles were removed under reduced pressure. The residue was extracted with hexane, the extract was filtered and the volatiles were removed under reduced pressure to leave a dark green-brown powder on the filter frit (1.297 g) and a sticky red-orange solid from the filtrate.

EXAMPLE 12

Preparation of {dimethylsilyl-N-(trans-1,4-cyclohexylene)-(tetramethylcyclopentadienyl)titanium dimethyl}bis-

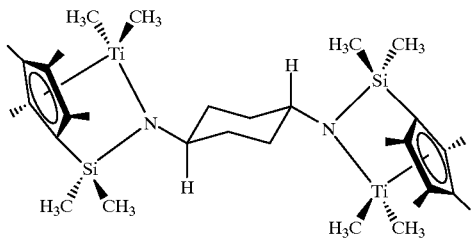

To a slurry of {dimethylsilyl-N-(trans-1,4-cyclohexyl)-(tetramethylcyclopentadienyl)titanium dichloride}bis- (0.367 g, 0.52 mmol) in 30 mL of diethyl ether was added MeMgBr (3.00 M in ether, 0.695 mL, 2.08 mmol) via syringe and the resulting mixture was stirred for 1 h at room temperature. The diluent of the black suspension was removed under reduced pressure and the residue was extracted with 40 mL of hexane. The hexane insoluble fraction was extracted with 20 mL of toluene, filtered, and the solvent removed to produce 0.12 g of crude product. The crude product was further washed with hexane and dried under vacuum for 2 h to give the desired product as a black solid.

$^1$H NMR ($C_6D_6$, 23° C.): δ 4.89 (s br, 2 H), 1.69 (m, 8 H), 2.00 (s, 12 H, $Me_4C_5$), 1.90 (s, 12 H, $Me_4C_5$), 0.51 (s, 12 H, $TiMe_2$), 0.42 (s, 12 H, $SiMe_2$). $^{13}$C NMR ($C_6D_6$, 23° C.): δ 60.75, 49.65, 47.16, 38.13, 31.91, 15.13, 14.31, 11.92, 5.41.

EXAMPLE 13

Preparation of {(methyl)(methylene)silyl-N-(t-butyl)(tetramethylcyclopentadienyl)titaniumdiiodide}bis-

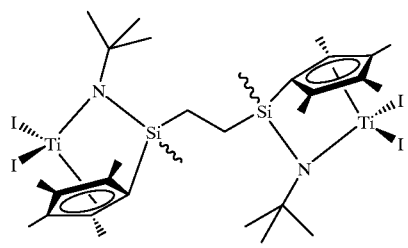

To a pre-cooled (−35° C.) toluene solution (30 mL) of {(methyl)(methylene)silyl-N-(t-butyl)(tetramethylcyclopentadienyl)titaniumdibenzyl}bis- (0.50 g, 0.50 mmol, Example 8) was added dropwise a pre-cooled (−35° C.) solution of $I_2$ (0.505 g, 1.99 mmol) in toluene (15 mL). The mixture was warmed gradually to room temperature and stirred overnight. The volatiles were removed under reduced pressure to leave an oily brown solid. The residue was extracted with hexane (2×20 mL) and filtered to give a brown solid and a dark brown filtrate. The solid was dried under reduced pressure to give 0.27 g of the desired product as two diastereomers in a 70:30 ratio.

Spectroscopic data for the major isomer of (1,2-$CH_2CH_2$){MeSi)(N-$^t$Bu)($η^5$-$Me_4C_5$)$TiI_2$}$_2$ are as follows. $^1$H NMR ($C_6D_6$, 23° C.): δ 2.34 (s, 6 H, $Me_4C_5$), 2.30 (s, 6 H, $Me_4C_5$), 1.98 (s, 6 H, $Me_4C_5$), 1.95 (s, 6 H, $Me_4C_5$), 1.69 (s, 18 H, $^t$Bu), 1.56 (t, 4 H, $C_2H_4$), 0.52 (s, 6 H, $SiMe_2$).

EXAMPLE 14

Preparation of {(methyl)(hexan-1,6-diyl)silyl-N-(t-butyl)(tetramethylcyclopentadienyl)-titanium diiodide}bis-

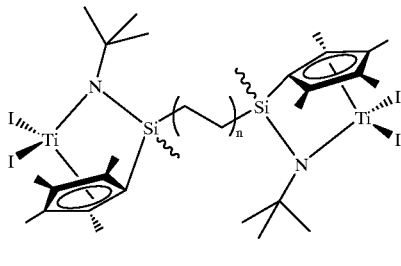

n = 3

To a pre-cooled (−35° C.) toluene solution (40 mL) of {(methyl)(hexan-1,6-diyl)silyl-N-(t-butyl)-(tetramethylcyclopentadienyl)titanium dibenzyl (0.817 g, 0.81 mmol, Example 7) was added dropwise a pre-cooled (−35° C.) solution of $I_2$ (0.819 g, 3.22 mmol) in toluene (20 mL). The mixture was warmed gradually to room temperature and stirred overnight. The volatiles were removed under reduced pressure to leave an oily brown solid. The residue was taken up with hexane (60 mL) and stirred for 30 min. The supernatant was decanted to leave a sticky brown solid. The residue was washed with hexane again and dried in vacuo to afford 0.55 g of the desired product as a sticky brown solid.

Spectroscopic data for the major isomer are as follows. $^1$H NMR ($C_6D_6$, 23° C.): δ 2.33 (s, 6 H, $Me_4C_5$), 2.31 (s, 6 H, $Me_4C_5$), 1.99 (s, 6 H, $Me_4C_5$), 1.68 (s, 18 H, $^t$Bu), 1.55–1.22 (m, 12 H, $C_6H_{12}$), 0.48 (s, 6 H, $SiMe_2$).

EXAMPLE 15

Preparation of {(methyl)(methylene)silyl-N-(t-butyl)-(tetramethylcyclopentadienyl)titanium dimethyl}bis-

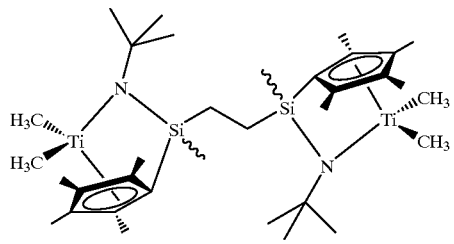

To a slurry of {(methyl)(methylene)silyl-N-(t-butyl)-(tetramethylcyclopentadienyl)titanium diiodide}bis- (0.220 g, 0.20 mmol, Example 13) in 20 mL of diethyl ether was added dropwise MeMgBr (3.00 M in ether, 0.273 mL, 0.82 mmol) via syringe and the resulting mixture was stirred for 1 h at room temperature. The solvent of the resulting suspension was removed under reduced pressure and the residue was extracted with 2×20 mL of hexane and filtered twice through Celite filtering aid. The solvent of the filtrate was removed under reduced pressure to afford 0.10 g of the desired product as a yellow green solid.

Spectroscopic data for the major isomer of {(methyl)(methylene)silyl-N-(t-butyl)(tetramethylcyclopentadienyl)

41 titanium dimethyl}bis- are as follows. $^1$H NMR (C$_6$D$_6$, 23° C.): δ 1.98 (s, 6 H, Me$_4$C$_5$), 1.96 (s, 6 H, Me$_4$C$_5$), 1.91 (s, 6 H, Me$_4$C$_5$), 1.87 (s, 6 H, Me$_4$C$_5$), 1.60 (s, 18 H, $^t$Bu), 1.58 (4 H, C$_2$H$_4$), 0.56 (s, 6 H, TiMe$_2$), 0.53 (s, 6 H, SiMe$_2$), 0.51 (s, 6 H, TiMe$_2$).

EXAMPLE 16

Preparation of {methyl(hexan-1,6-diyl)silyl-N-(t-butyl)-(tetramethylcyclopentadienyl)titanium dimethyl}bis-

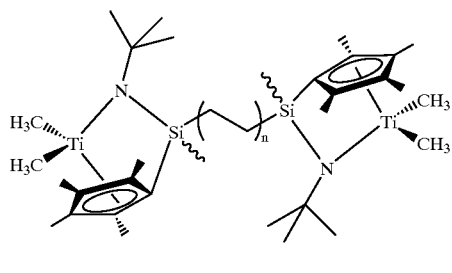

n = 3

To a slurry of (methyl(hexan-1,6-diyl)silyl-N-(t-butyl)-(tetramethylcyclopentadienyl)titanium diiodide}bis- (0.550 g, 0.48 mmol, Example 14) in 30 mL of diethyl ether was added dropwise MeMgBr (3.00 M in ether, 0.650 mL, 1.95 mmol) via syringe and the resulting mixture was stirred for 1 h at room temperature. The diluent of the resulting suspension was removed under reduced pressure and the residue was extracted with 2×20 mL of hexane and filtered twice through diatomaceous earth filtering aid. The solvent of the filtrate was removed under reduced pressure to afford 0.25 g of an isomeric mixture of the desired product as a yellow green solid.

Spectroscopic data for the major isomer of {methyl(hexan-1,6-diyl)silyl-N-(t-butyl)-(tetramethylcyclopentadienyl)titanium dimethyl}bis- are as follows. $^1$H NMR (C$_6$D$_6$, 23° C.): δ 1.98 (s, 6 H, Me$_4$C$_5$), 1.96 (s, 6 H, Me$_4$C$_5$), 1.89 (s, 6 H, Me$_4$C$_5$), 1.86 (s, 6 H, Me$_4$C$_5$), 1.59 (s, 18 H, $^t$Bu), 1.64–1.52, 1.16 (m, 12 H, C$_6$H$_{12}$), 0.51 (s, 6 H, TiMe$_2$), 0.50 (s, 6 H, SiMe$_2$), 0.48 (s, 6 H, TiMe$_2$).

EXAMPLE 17

Titanium, diiodide(N-(1,1-dimethylethyl)-1-((1,2,3,3a,7a-η)-1H-inden-1-yl)-1,1-dimethylsilanaminato(2)N)(2,2'-(1,5-pentanediyl)bis-

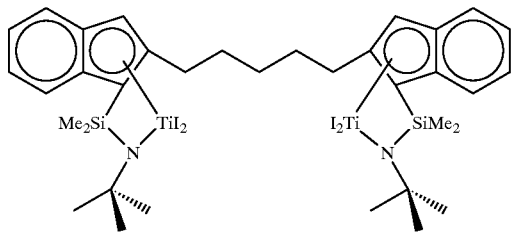

Titanium, dimethyl(N-(1,1-dimethylethyl)-1-((1,2,3,3a,7a-η)-1H-inden-1-yl)-1,1-dimethylsilanaminato(2-)-N)(2,2'-(1,5-pentanediyl)bis- (prepared by methylation of the tetrachloride complex of Example 1) is converted to the tetraiodide derivative by treatment with 4 equivalents of iodine in diethylether suspension, followed by work up. Due to the reduced solubility in hydrocarbons, highly pure crystals of the tetraiodide compound are recovered. This product may be reconverted to highly pure tetramethyl- or other hydrocarbyl derivative.

EXAMPLE 18

Highly pure titanium, dimethylN-(1,1-dimethylethyl-1-((1,2,3,3a,7a-η-1H-inden-1-yl)-1,1-dimethylsilanaminato(2-)-N)(2,2'-(1,5-pentanediyl) bis- To a slurry of titanium, diiodide(N-$^t$Bu)-1-((1,2,3,3a,7a-η)-1H-inden-1-yl)-1,1-dimethylsilanaminato(2-)-N)(2,2'-(1,5-pentanediyl)bis- (2.00 g, 1.73 mmol, Example 17) in 30 mL of hexanes was added dropwise MeMgBr (3.00 M in diethyl ether, 2.90 mL, 8.65 mmol) via syringe and the resulting mixture was allowed to warm to room temperature and stirred for additional 2 h. The solvent of the resulting suspension was removed under reduced pressure and the residue was extracted with 2×20 mL of hexane and filtered twice through fine glass frits using a diatomaceous earth filtering aid. The solvent of the filtrate was removed under reduced pressure to afford 1.15 g of the desired product as a yellow oily solid.

Two isomers were observed in 1:1 ratio. $^1$H NMR (C$_6$D$_6$): 7.53, 7.44, 7.05, 6.84 (m, 8 H), 6.82 (brs, 2 H), 2.44, 2.31 (m, 4 H), 1.62 (m, 4 H), 1.43 (brs, 18 H), 1.33 (m, 2 H), 0.83 (brs, 6 H), 0.54, 0.53 (brs, 12 H), −0.13 (brs, 6 H). $^{13}$C{$^1$H} (C$_6$D$_6$): 146.9, 134.7, 132.0, 125.7(m), 125.3 (m), 115.2, 115.1, 88.7, 58.1, 57.1, 52.0, 51.9, 34.4, 32.8, 32.7, 29.5, 6.28, 5.69.

EXAMPLE 19

Activation of titanium, dimethyl(N-$^t$Bu)-1-((1,2,3,3a,7a-η)-1H-inden-1-yl)-1,1-dimethylsilanaminato (2-)-N)(2,2'-(1,5-pentanediyl)bis-(Example 18) with two equivalents of tris(pentafluorophenyl)aluminum (FAAL)

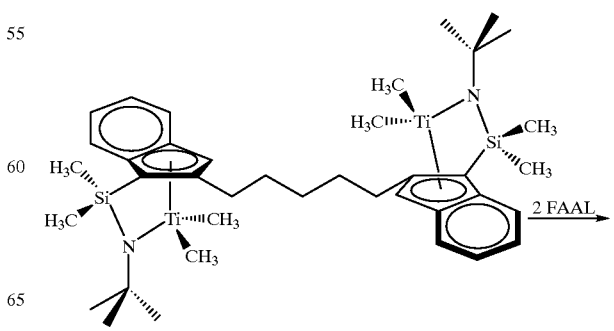

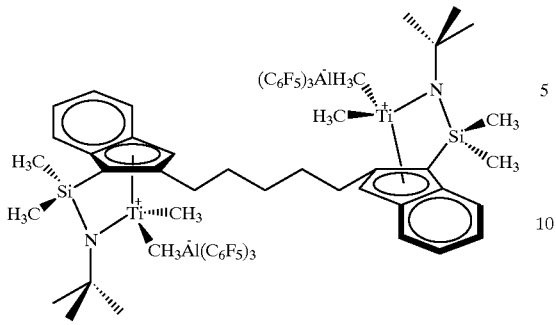
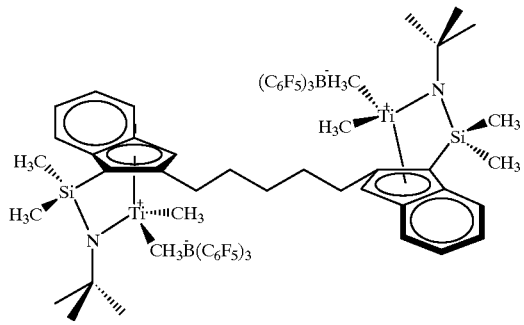

NMR reactions were carried out in J-Young NMR tubes or NMR tubes with good seals, and the samples were loaded into the NMR tubes in a glove box after mixing the above two reagents in 0.7 mL of benzene-$d_6$ in a 1:2 ratio (0.02 mmol scale). The mixture was allowed to react at room temperature for 10 min before the NMR spectra were recorded. An orange solution was observed immediately after the mixing and the NMR data are consistent with the structure shown in the above equation (as three diastereomers). This species, titanium, [($\mu$-Me)Al$^-$(C$_6$F$_5$)$_3$](methyl)(N-$^t$Bu)-1-((1,2,3,3a,7a-$\eta$)-1H-inden-1-yl)-1,1-dimethylsilanaminato(2-)-N)(2,2'-(1,5-pentanediyl)bis-, has a half-life of about 48 h at room temperature.

Some key spectroscopic data for the above active dicationic species (titanium, [($\mu t$-Me)Al$^-$(C$_6$F$_5$)$_3$](methyl)(N-$^t$Bu)-1-((1,2,3,3a,7a-$\eta$)-1H-inden-1-yl)-1,1-dimethylsilanaminato(2-)-N)(2,2'-(1,5-pentanediyl)bis-) are as follows. $^1$H NMR (C$_6$D$_6$, 23° C.): δ 1.29 (s, 3 H, TiMe), 0.20 (s, 3 H, TiMe), −0.43 (s br, 6 H, Al-$\mu$-Me). $^{19}$F NMR (C$_6$D$_6$, 23° C.): δ −122.79 (d, $^3J_{F-F}$=15.3 Hz, 12 F, oF), −153.47, 153.72, 154.06 (t, 6 F, p-F), −161.53, 161.90 (m, 12 F, m-F).

EXAMPLE 20

Activation of titanium, dimethyl(N-$^t$Bu)-1-((1,2,3,3a,7a-$\eta$)-1H-inden-1-yl)-1,1-dimethylsilanaminato(2-)-N)(2,2'-(1,5-pentanediyl)bis-(Example 18) with two equivalents of tris(pentafluorophenyl)borane (FAB)

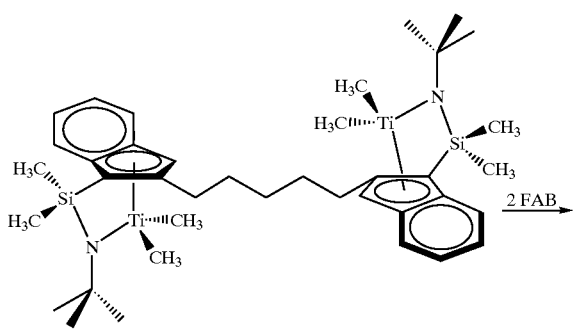

NMR reactions were carried out in J-Young NMR tubes or NMR tubes with good seals, and the samples were loaded into the NMR tubes in a glove box after mixing the above two reagents in 0.7 mL of benzene-$d_6$ in a 1:2 ratio (0.02 mmol scale). The mixture was allowed to react at room temperature for 10 min before the NMR spectra were recorded. An orange red solution was observed immediately after the mixing and the NMR data are consistent with the structure shown in the above equation (as three diastereomers). This species, titanium, [($\mu$-Me)B$^-$(C$_6$F$_5$)$_3$]methyl(N-$^t$Bu)-1-((1,2,3,3a,7a-$\eta$)-1H-inden-1-yl)-1,1-dimethylsilanaminato(2-)-N)(2,2'-(1,5-pentanediyl)bis-, has a half-life of about 19 h at room temperature.

EXAMPLE 21

Reaction of titanium, dimethyl(N-$^t$Bu)-1-((1,2,3,3a,7a-$\eta$)-1H-inden-1-yl)-1,1-dimethylsilanaminato(2-)-N)(2,2'-(1,5-pentanediyl)bis-(Example 18) with four equivalents of tris(pentafluorophenyl)aluminum (FAAL).

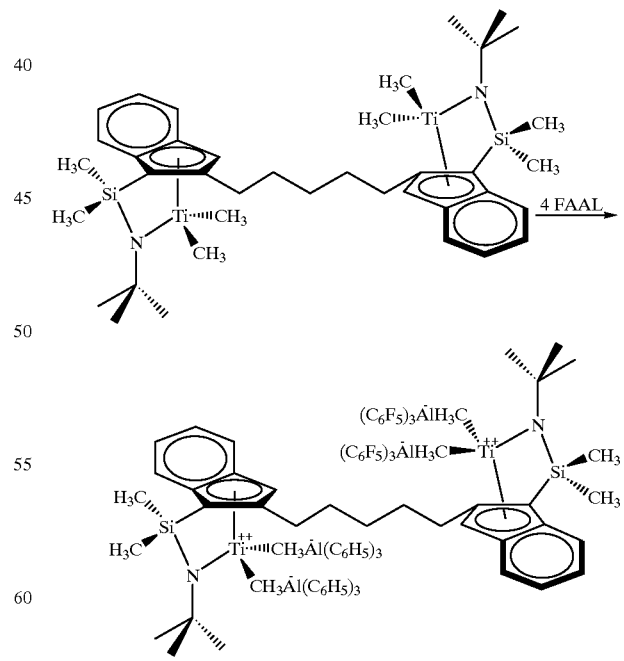

NMR reactions were carried out in J-Young NMR tubes or NMR tubes with good seals, and the samples were loaded into the NMR tubes in a glove box after mixing the above two reagents in 0.7 mL of benzene-$d_6$ in a 1:4 ratio (0.02 mmol scale). The mixture was allowed to react at room temperature for 10 min before the NMR spectra were recorded. A deep red solution was observed immediately after the mixing and the NMR data are consistent with the structure shown in the above equation, titanium, di[($\mu$-Me)Al⁻($C_6F_5$)$_3$] (N-$^t$Bu)-1-((1,2,3,3a,7a-$\eta$)-1H-inden-1-yl)-1,1-dimethylsilanaminato(2-)-N)(2,2'-(1,5-pentanediyl)bis-. This species has a half-life of about 8 h at room temperature.

Some key spectroscopic data for the above formally tetracationic or bis(dopple-zwitterionic) species are as follows. $^1$H NMR ($C_6D_6$, 23° C.): $\delta$ −0.04 (s br, Al-$\mu$-Me), −0.32 (s br, Al-$\mu$-Me). $^{19}$F NMR ($C_6D_6$, 23° C.): $\delta$ −122.92 (d, $^3J_{F-F}$=15.3 Hz, 24 F, o-F), −152.44 (s br, 12 F, p-F), −161.18 (s br, 24 F, m-F).

Polymerization 3

All feeds were passed through columns of alumina and a decontaminant (Q-5™ catalyst available from Englehardt Chemicals Inc.) prior to introduction into the reactor. Catalyst and cocatalyst (activator) are handled in a glovebox containing an atmosphere of argon or nitrogen. A stirred 2.0 liter reactor is charged with about 740 g of mixed alkanes solvent and 118 g of 1-octene comonomer. Hydrogen is added as a molecular weight control agent by differential pressure expansion from a 75 ml addition tank at 25 psi (2070 kPa). The reactor is heated to the polymerization temperature of 140° C. and saturated with ethylene at 500 psig (3.4 MPa). Catalysts and cocatalyst as dilute solutions in toluene, were mixed and transferred to a catalyst addition tank and injected into the reactor. The polymerization conditions were maintained for 15 minutes with ethylene added on demand. The resulting solution was removed from the reactor, and 10 ml of a toluene solution containing approximately 67 mg of a hindered phenol antioxidant (Irganox™ 1010 from Ciba Geigy Corporation) and 133 mg of a phosphorus stabilizer (Irgafos™ 168 from Ciba Geigy Corporation) were then added.

Between polymerization runs a wash cycle was conducted in which 850 g of mixed alkanes were added to the reactor and the reactor heated to 150° C. The reactor was then emptied of the heated solvent immediately before beginning a new polymerization run.

Polymers were recovered by drying in a vacuum oven set at 140° C. for about 20 hours. Density values are derived by determining the polymers mass when in air and when immersed in methylethyl ketone. Micro melt index values (MMI) are obtained using a Custom Scientific Instrument Inc. Model CS-127MF-015 apparatus at 190° C., and are unit-less values calculated as follows: MMI=1/(0.00343 t−0.00251), where t=time in seconds as measured by the instrument. Results are contained in Table 3.

TABLE 3

| Run | Catalyst/Activator ($\mu$mole/$\mu$mole) | Yield (g) | Eff.[1] | Density g/ml | MMI[2] | Mw (10³) | PDI[3] |
|---|---|---|---|---|---|---|---|
| 12* | TTiMe⁴/A (0.6/0.6) | 120.2 | 4.18 | 0.899 | 8.1 | 72.0 | 2.10 |
| 13 | Ex. 18⁵/A (0.4/0.8) | 82.7 | 2.16 | 0.881 | 0.5 | 131.0 | 2.25 |
| 14 | Ex. 18⁵/B (0.4/0.8) | 26.6 | 0.69 | 0.881 | 0.7 | 126.0 | 2.23 |
| 15 | Ex. 18⁵/C 1.0/8.0) | 55.6 | 0.58 | 0.882 | 0.4 | 143.0 | 2.29 |
| 16 | Ex. 12⁶/A (5.0/10) | 46.8 | 0.1 | 0.867 | 1.9 | 113.0 | 2.25 |
| 17 | Ex. 15⁷/D (5.0/10) | 146.3 | 3.82 | 0.897 | 3.0 | 91.1 | 2.17 |
| 18 | Ex. 16⁸/D (5.0/10) | 98.7 | 2.06 | 0.898 | 0.8 | 133.3 | 2.16 |

TABLE 3-continued

| Run | Catalyst/Activator ($\mu$mole/$\mu$mole) | Yield (g) | Eff.[1] | Density g/ml | MMI[2] | Mw (10³) | PDI[3] |
|---|---|---|---|---|---|---|---|
| 19* | TTiMe⁴/D (0.75/0.75) | 150.5 | 4.19 | 0.897 | 3.5 | 86.3 | 2.08 |

*not an example of the invention
[1] efficiency, g polymer/$\mu$g metal
[2] melt index, dg/min, measured by micromelt indexer
[3] polydispersity index (Mw/Mn)
[4] (t-butylamido)dimethyl(tetramethylcyclopentadienyl)silanetitanium dimethyl
[5] titanium, dimethyl(N-$^t$Bu)-1-((1,2,3,3a,7a-$\eta$)-1H-inden-1-yl)-1,1-dimethylsilanaminato(2-)-N)(2,2'-(1,5-pentanediyl)bis-
[6] {dimethylsilyl-N-(trans-1,4-cyclohexylene)(tetramethylcyclopentadienyl) titanium dimethyl}bis-
[7] {methyl(methylene)silyl-N-(t-butyl)-(tetramethylcyclopentadienyl)titanium dimethyl}bis-
[8] {(methyl)(1,6-hexandiyl)silyl-N-(t-butyl)-(tetramethylcyclopentadienyl) titanium dimethyl}bis-
A = methyldi($C_{14-20}$ alkyl)ammonium tetrakis(pentafluorophenyl)borate
B = tris(pentafluorophenyl)borane (FAB)
C = tris(pentafluorophenyl)alumane (FAAL)
D = methyldi($C_{14-20}$ alkyl)ammonium bis(tris(pentafluorophenyl) aluminum)-2-undecylimidazolide

What is claimed is:
1. A composition comprising:
1) one or more bimetallic complexes corresponding to the formula:

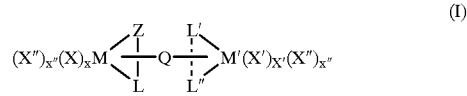

(I)

wherein:
M and M' are independently Group 3, 4, 5, 6, or Lanthanide metals;
L is a divalent group (or trivalent group if bound to Q) having up to 50 nonhydrogen atoms and containing an aromatic $\pi$-system through which the group is bound to M, said L also being bound to Z;
L' is a monovalent group or a divalent group (if bound to L" or Q), or a trivalent group (if bound to both L" and Q) having up to 50 nonhydrogen atoms and containing an aromatic $\pi$-system through which the group is bound to M';
L" is a monovalent group or a divalent group (if bound to L' or Q), or a trivalent group (if bound to both L' and Q) having up to 50 nonhydrogen atoms and containing an aromatic $\pi$-system through which the group is bound to M', or L" is a moiety comprising boron or a member of Group 14 of the Periodic Table of the Elements, and optionally also comprising nitrogen, phosphorus, sulfur or oxygen, said L" having up to 20 non-hydrogen atoms;
Z is a moiety comprising boron or a member of Group 14 of the Periodic Table of the Elements, and also comprising nitrogen, phosphorus, sulfur or oxygen, said Z having up to 20 non-hydrogen atoms;
X and X' independently each occurrence are anionic ligand groups having up to 40 atoms exclusive of ligands containing an aromatic or conjugated dienyl $\pi$-system through which the group is bound to M and M', respectively, or optionally two X groups or two X' groups together form a divalent, $C_{4-40}$ conjugated or nonconjugated dienyl ligand, optionally substituted with one or more hydrocarbyl, silyl, halocarbyl, or halohydrocarbyl groups, that together with M and M', respectively, form a metallocyclopentene moiety; or further optionally, two X groups or two X' groups together form a neutral, $C_{4-40}$ conjugated or nonconjugated diene ligand, optionally substituted with one or more hydrocarbyl, silyl, halocarbyl, or halohydrocarbyl groups, that is π-bonded to M and M', respectively;

X" independently each occurrence is a neutral ligating compound having up to 20 atoms, exclusive of neutral dienes;

Q is a divalent anionic ligand group bound at one terminus to either Z or L and bound at the remaining terminus to either L' or L", said Q having up to 20 nonhydrogen atoms; and x, x', and x" are independently integers from 0 to 3; and 2) one or more activating cocatalysts;

wherein activating cocatalyst component 2) causes both metal centers, M and M', of the one or more bimetallic metal complexes 1) to be catalytically active for the polymerization of addition polymerizable monomers.

2. A composition according to claim 1 wherein the at least one bimetallic complex of component 1) corresponds to the following formula II:

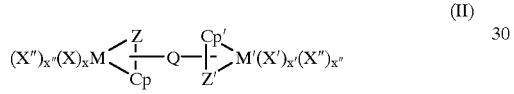
(II)

wherein Z, M, M', X, X', X", x, x', and x" are as previously defined in claim 1;

Z' is a moiety comprising boron or a member of Group 14 of the Periodic Table of the Elements, and also comprising nitrogen, phosphorus, sulfur or oxygen, said Z' having up to 20 non-hydrogen atoms;

Cp and Cp' are cyclic $C_5R'_4$ groups bound to Z and Z' respectively and bound to M and M' respectively by means of delocalized π-electrons, wherein R', independently each occurrence, is hydrogen, hydrocarbyl, silyl, halogen, fluorohydrocarbyl, hydrocarbyloxy, hydrocarbylsiloxy, N,N-di(hydrocarbylsilyl)amino, N-hydrocarbyl-N-silylamino, N,N-di(hydrocarbyl)amino, hydrocarbyleneamino, di(hydrocarbyl) phosphino, hydrocarbylsulfido; or hydrocarbyloxy-substituted hydrocarbyl, said R' having up to 20 nonhydrogen atoms, and optionally, two such R' substituents may be joined together thereby causing Cp or Cp' to have a fused ring structure, or further optionally, Cp or Cp' each independently is a trivalent derivative of the above identified $C_5R'_4$ group that is also bonded to Q and one R' on each of Cp or Cp' is a covalent bond to Q;

Q is S, P, or a linear or cyclic hydrocarbylene or silanediyl group or nitrogen, oxygen, or halo substituted derivative thereof, said Q having up to 20 nonhydrogen atoms.

3. A composition according to claim 1 wherein the at least one bimetallic complex of component 1) corresponds to the following formula III:

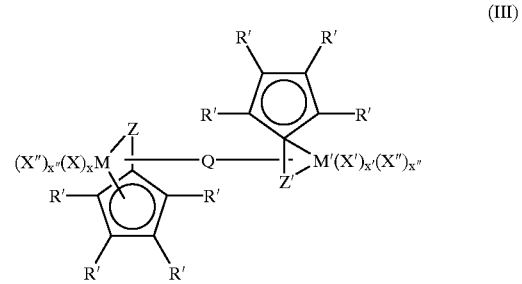
(III)

wherein:

M and M' independently each occurrence are Ti, Zr, Hf, Sc, yttrium, or La;

Q, X, X', X", x, x' and x" are as previously defined in claim 1;

R' each occurrence is hydrogen, hydrocarbyl, silyl, germyl, halo, cyano, halohydrocarbyl, hydrocarbyloxy, hydrocarbylsiloxy, di(hydrocarbylsilyl)amino, hydrocarbylsilylamino, di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two R' groups together form a divalent derivative thereof connected to adjacent positions of the cyclopentadienyl ring thereby forming a fused ring structure, or R' in one occurrence per cyclopentadienyl system is a covalent bond to Q;

Z and Z' independently each occurrence are —Z*Y'—, wherein:

Y' is —O—, —S—, —NR"—, —PR"—, —OR", or —NR"$_2$ (and with respect to —OR" and —NR"$_2$, one bond is a dative bond through the available electron pair), wherein R" is hydrogen, hydrocarbyl, silyl, or silylhydrocarbyl of up to 12 nonhydrogen atoms, or R" is a covalent bond to Q, and Z* is SiR*$_2$, CR*$_2$, SiR*$_2$SiR*$_2$, CR*$_2$CR*$_2$, CR*=CR*, CR*$_2$SiR*$_2$, or GeR*$_2$;

wherein R* each occurrence is independently hydrogen, hydrocarbyl, silyl, halogenated alkyl, or halogenated aryl, said R* having up to 12 non-hydrogen atoms.

4. A composition according to claim 1 wherein the at least one bimetallic complex of component 1) corresponds to the following formula (IV):

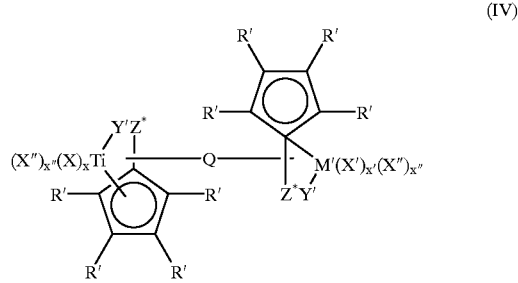
(IV)

wherein:

Q is a linear or cyclic hydrocarbylene or silanediyl group, or a nitrogen or oxygen containing derivative thereof, M' is Ti, Zr or Hf;

R' each occurrence is hydrogen, hydrocarbyl, silyl, germyl, halo, cyano, halohydrocarbyl, hydrocarbyloxy, hydrocarbylsiloxy, di(hydrocarbylsilyl)amino, hydrocarbylsilylamino, di(hydrocarbyl)amino, hydrocarbyleneamino, di(hydrocarbyl)phosphino, hydrocarbylsulfido; or hydrocarbyloxy-substituted hydrocarbyl, said R' having up to 20 nonhydrogen atoms, and optionally, two R' groups together form a divalent derivative thereof connected to adjacent positions of the cyclopentadienyl ring thereby forming a fused ring structure, or R' in one occurrence per cyclopentadienyl system is a covalent bond to Q;

X and X' are halide, $C_{1-10}$ hydrocarbyl, or di($C_{1-10}$ hydrocarbyl)amido; and Y'Z* is: —NR"—(ER"')m— wherein:

E is independently each occurrence silicon or carbon;

R" is $C_{1-10}$ hydrocarbyl or a covalent bond to Q;

R"' is $C_{1-4}$ alkyl, phenyl, or a covalent bond to Q; and m is an integer from 1 to 10.

5. A composition according to claim 4 wherein R' independently each occurrence is hydrogen, hydrocarbyl, silyl, fluorophenyl, hydrocarbyloxy, N,N-di(hydrocarbyl)amino, hydrocarbyleneamino, or hydrocarbyloxy-substituted hydrocarbyl, said R' having up to 20 non-hydrogen atoms, or two adjacent R' groups are joined together forming part of a fused ring system.

6. A composition according to claim 5 wherein R' is hydrogen, methyl, ethyl, propyl, butyl, pentyl, hexyl, (including where appropriate all isomers), cyclopentyl, cyclohexyl, norbornyl, benzyl, phenyl, N,N-di(methyl) amino, pyrrolyl, pyrrolidinyl, piperidinyl, morpholinyl, or two R' groups are linked together, the entire $C_5R'_4$ group thereby forming an indenyl, tetrahydroindenyl, fluorenyl, tetrahydrofluorenyl, indacenyl, or octahydrofluorenyl group, or a $C_{1-6}$ hydrocarbyl-substituted, N,N-di(methyl)amino-substituted, or pyrrolyl-substituted derivative thereof.

7. The composition of claim 1 wherein the activating cocatalyst 2) is a Lewis acid present in an amount equal to at least a 2:1 molar ratio with the metal complex.

8. The composition of claim 1 wherein the activating cocatalyst 2) is tris(pentafluorophenyl)borane or tris (pentafluorophenyl)aluminum.

9. The composition of claim 7 wherein the activating cocatalyst 2) is present in an amount equal to at least a 4:1 molar ratio with the metal complex.

10. A metal complex corresponding to the following formula IA:

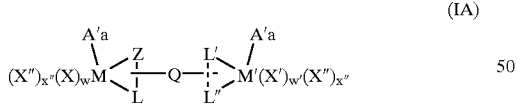

(IA)

wherein:

M and M' are independently Group 3, 4, 5, 6, or Lanthanide metals;

L is a divalent group (or trivalent group if bound to Q) having up to 50 nonhydrogen atoms and containing an aromatic π-system through which the group is bound to M, said L also being bound to Z;

L' is a monovalent group or a divalent group (if bound to L" or Q), or a trivalent group (if bound to both L" and Q) having up to 50 nonhydrogen atoms and containing an aromatic π-system through which the group is bound to M';

L" is a monovalent group or a divalent group (if bound to L' or Q), or a trivalent group (if bound to both L' and Q) having up to 50 nonhydrogen atoms and containing an aromatic π-system through which the group is bound to M', or L" is a moiety comprising boron or a member of Group 14 of the Periodic Table of the Elements, and optionally also comprising nitrogen, phosphorus, sulfur or oxygen, said L" having up to 20 non-hydrogen atoms;

Z is a moiety comprising boron or a member of Group 14 of the Periodic Table of the Elements, and also comprising nitrogen, phosphorus, sulfur or oxygen, said Z having up to 20 non-hydrogen atoms;

X and X' independently each occurrence are anionic ligand groups having up to 40 atoms exclusive of ligands containing an aromatic or conjugated dienyl π-system through which the group is bound to M and M', respectively, or optionally two X groups or two X' groups together form a divalent, $C_{4-40}$ conjugated or nonconjugated dienyl ligand, optionally substituted with one or more hydrocarbyl, silyl, halocarbyl, or halohydrocarbyl groups, that together with M and M', respectively, form a metallocyclopentene moiety; or further optionally, two X groups or two X' groups together form a neutral, $C_{4-40}$ conjugated or nonconjugated diene ligand, optionally substituted with one or more hydrocarbyl, silyl, halocarbyl, or halohydrocarbyl groups, that is π-bonded to M and M' respectively, X" independently each occurrence is a neutral ligating compound having up to 20 atoms, exclusive of neutral dienes;

Q is a divalent anionic ligand group bound at one terminus to either Z or L and bound at the remaining terminus to either L' or L", said Q having up to 20 nonhydrogen atoms; and w, w', are independently integers from 0 to 2 selected to provide charge neutrality, x" is an integer from 0 to 3;

A' independently each occurrence is the anionic or zwitterionic remnant of a cocatalyst component; and a, independently each occurrence, is 1 or 2.

11. A metal complex according to claim 10, corresponding to the formula:

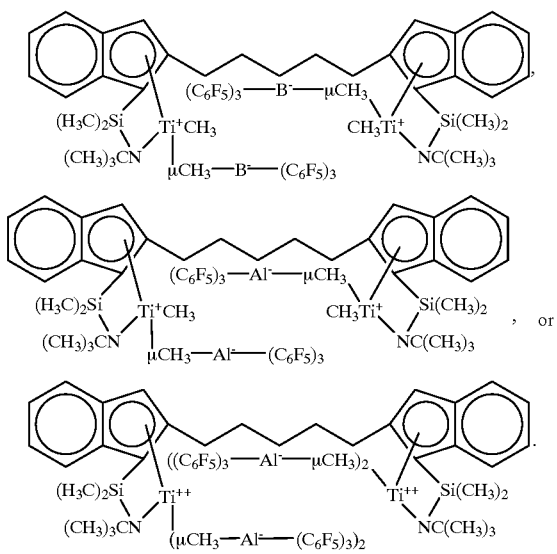

* * * * *